United States Patent [19]
Rennex

[11] Patent Number: 5,386,741
[45] Date of Patent: Feb. 7, 1995

[54] ROBOTIC SNAKE

[76] Inventor: Brian G. Rennex, 431 Muddy Branch Rd., #101, Gaithersburg, Md. 20878

[21] Appl. No.: 72,853

[22] Filed: Jun. 7, 1993

[51] Int. Cl.[6] .......................... A61B 1/00; B25J 3/00; B25J 17/00
[52] U.S. Cl. ........................ 74/490.05; 15/104.33; 74/490.03; 128/4; 299/31; 414/5; 901/22; 901/23; 901/28
[58] Field of Search ............ 74/479 BJ, 479 BP; 128/4; 15/104.05, 104.33; 299/31; 901/15, 22, 23, 28, 47; 414/5

[56] References Cited
U.S. PATENT DOCUMENTS

| | | | |
|---|---|---|---|
| 4,095,655 | 6/1978 | Still | 299/31 |
| 4,148,307 | 4/1979 | Utsugi | 128/4 |
| 4,302,138 | 11/1981 | Zarudiansky | 414/5 |
| 4,577,621 | 3/1986 | Patel | 128/4 |
| 5,129,279 | 7/1992 | Rennex | 74/479 BJ |
| 5,205,613 | 4/1993 | Brown, Jr. | 299/31 |

FOREIGN PATENT DOCUMENTS 1-216238  8/1989  Japan ........................ 128/4

Primary Examiner—Allan D. Herrmann

[57] ABSTRACT

This invention reveals improvements in a flexible robotic limb which can function as a robotic snake. These improvements are particularly pertinent to miniaturization applications such as catheters or positioners for microsurgery, micro-assembly, micro-manipulation, or micro-exploration. This invention developes detailed new component designs, and it combines the basic structure with systems for sensing, control, and signal transmission. These systems include pressure sensors, length sensors, protective skins, ultrasonic imagers, cutting tools, and multiplexing schemes.

33 Claims, 17 Drawing Sheets

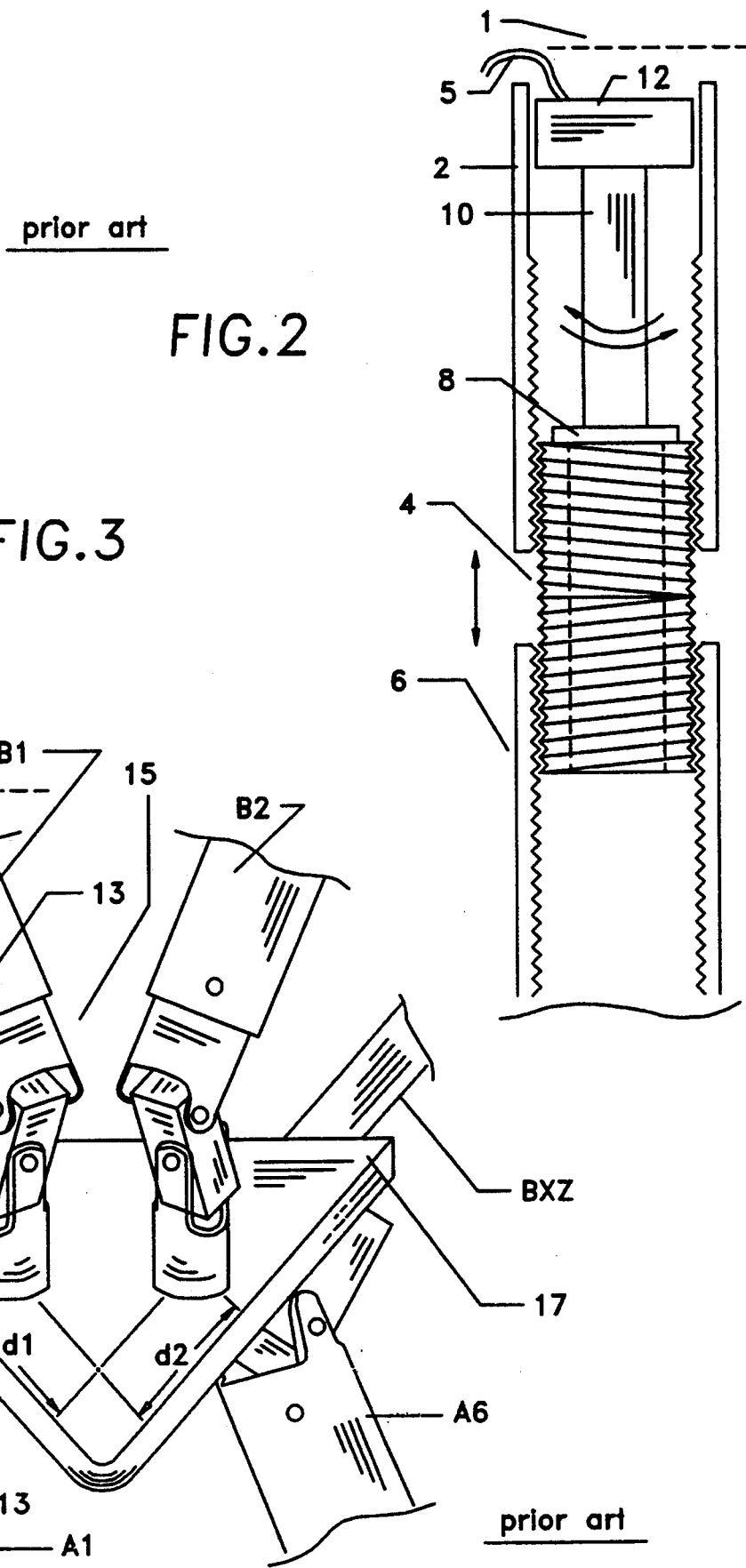

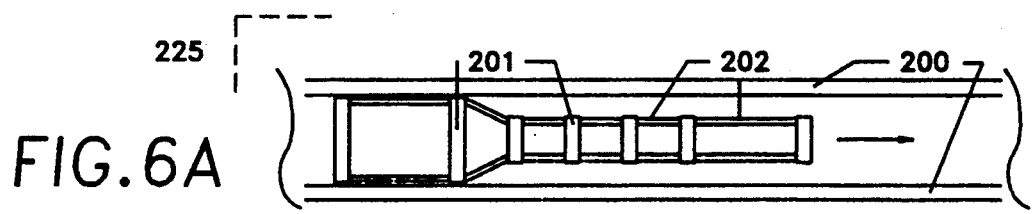
FIG.6A
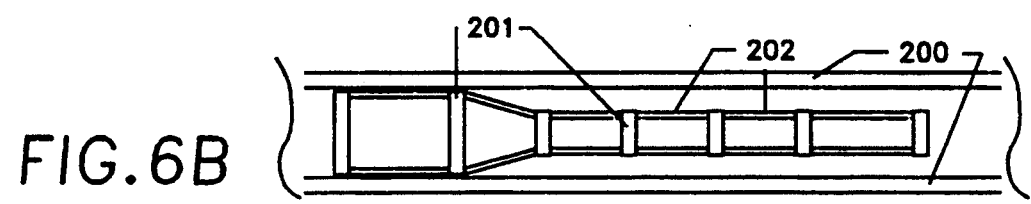
FIG.6B
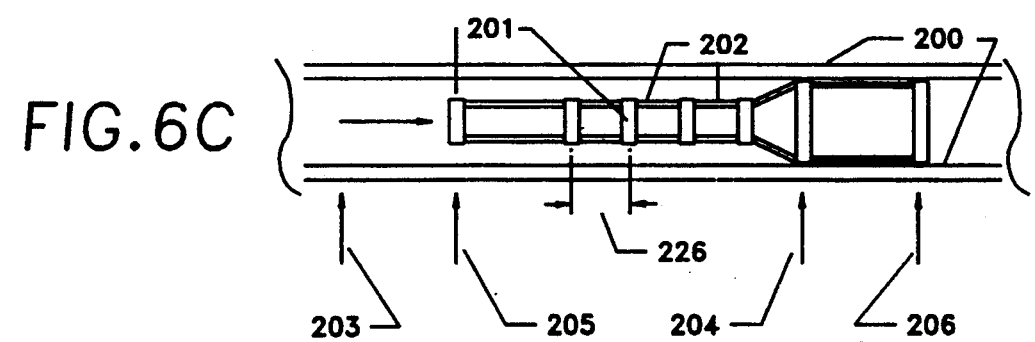
FIG.6C
FIG.6D
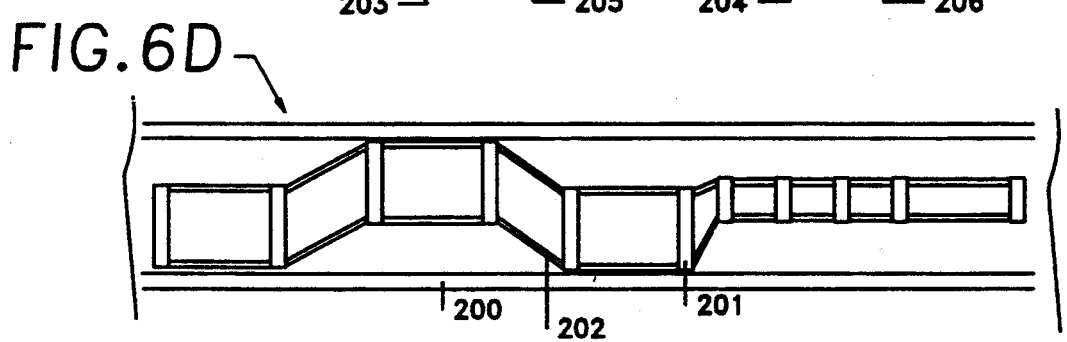
FIG.7
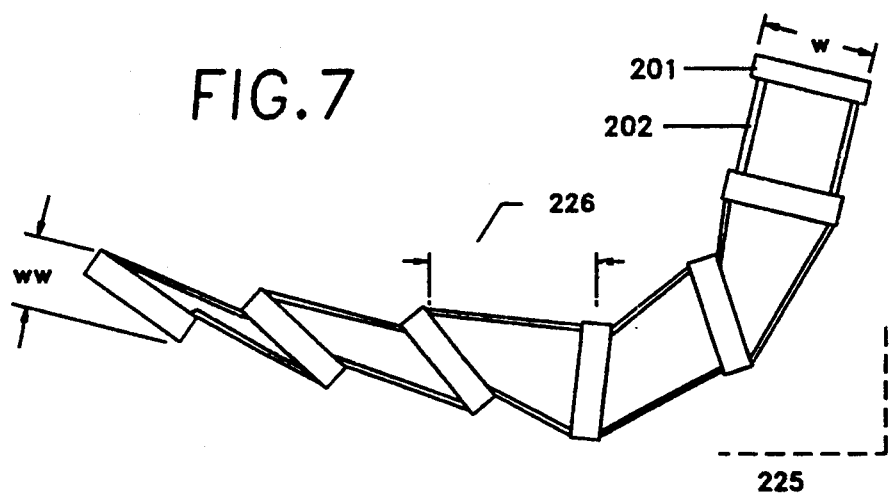

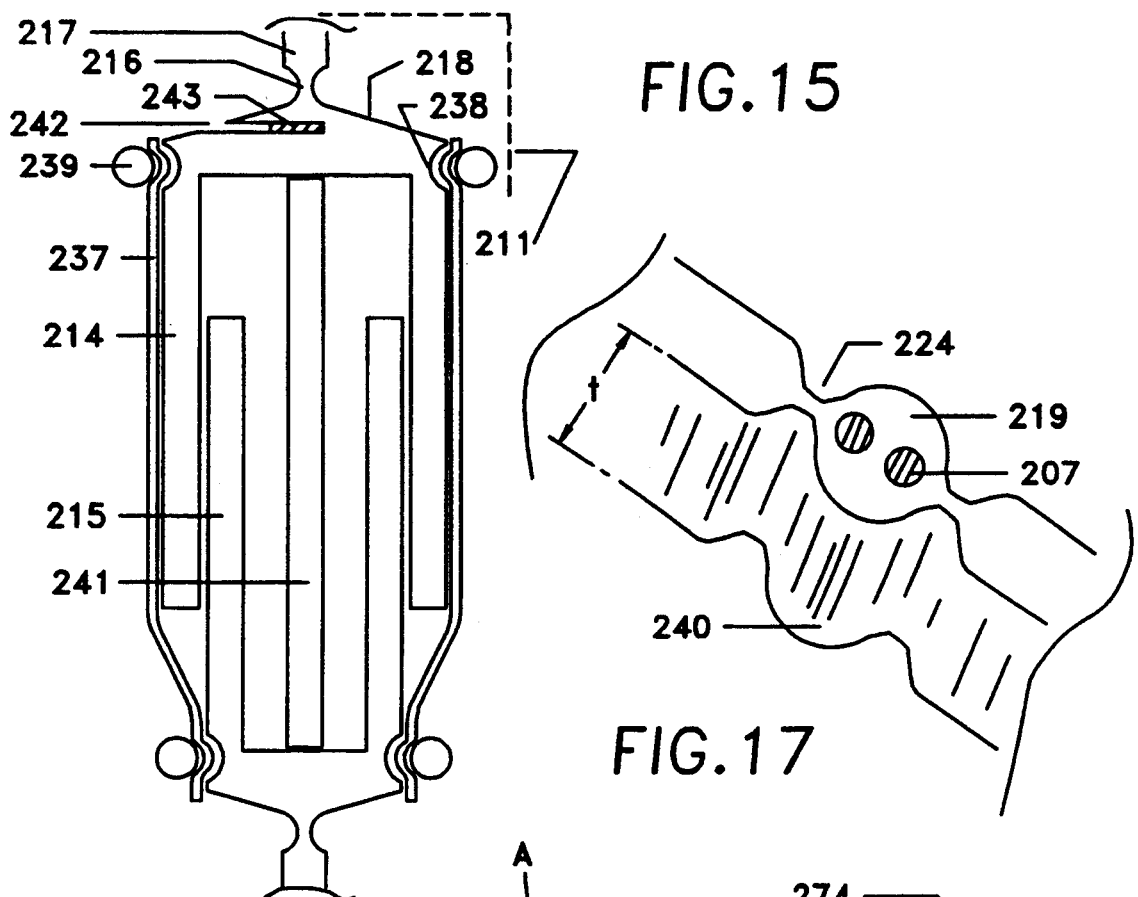
FIG. 15
FIG. 17
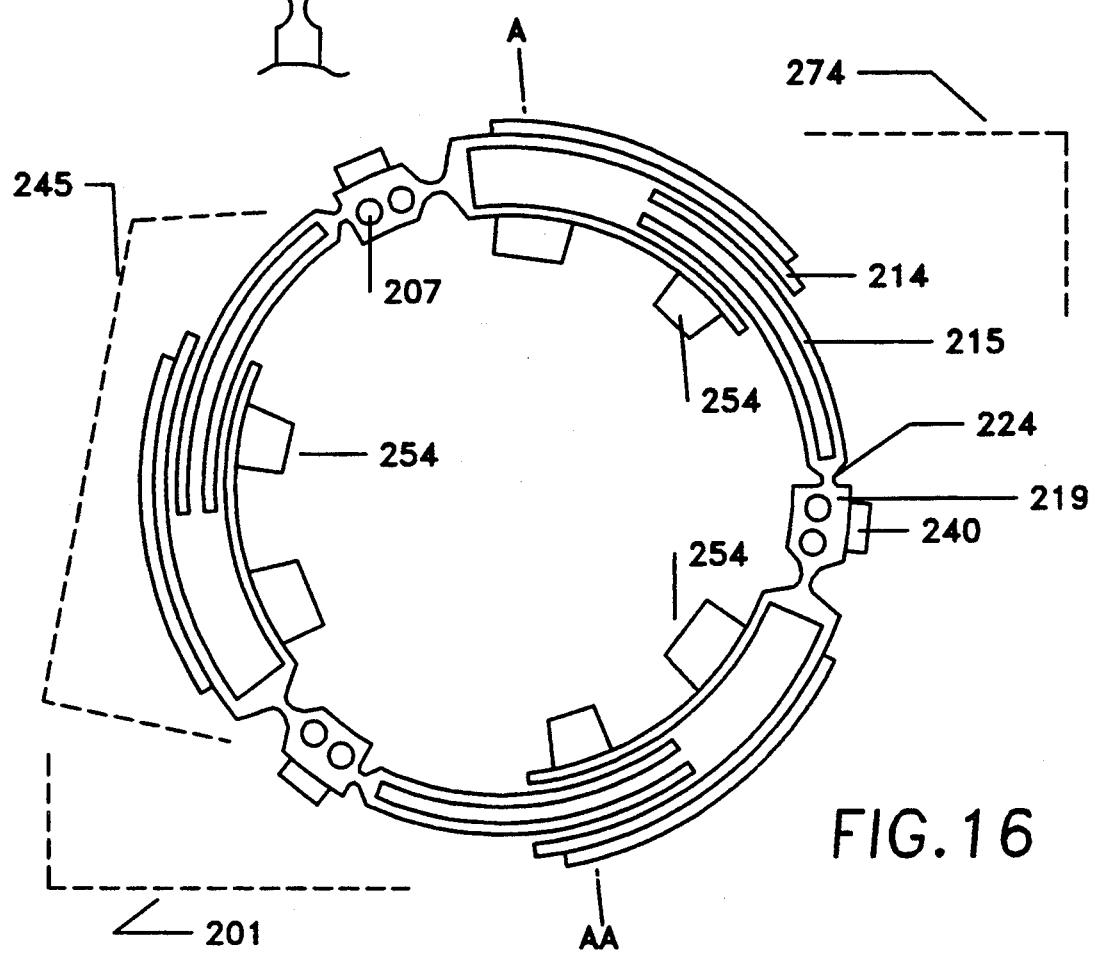
FIG. 16

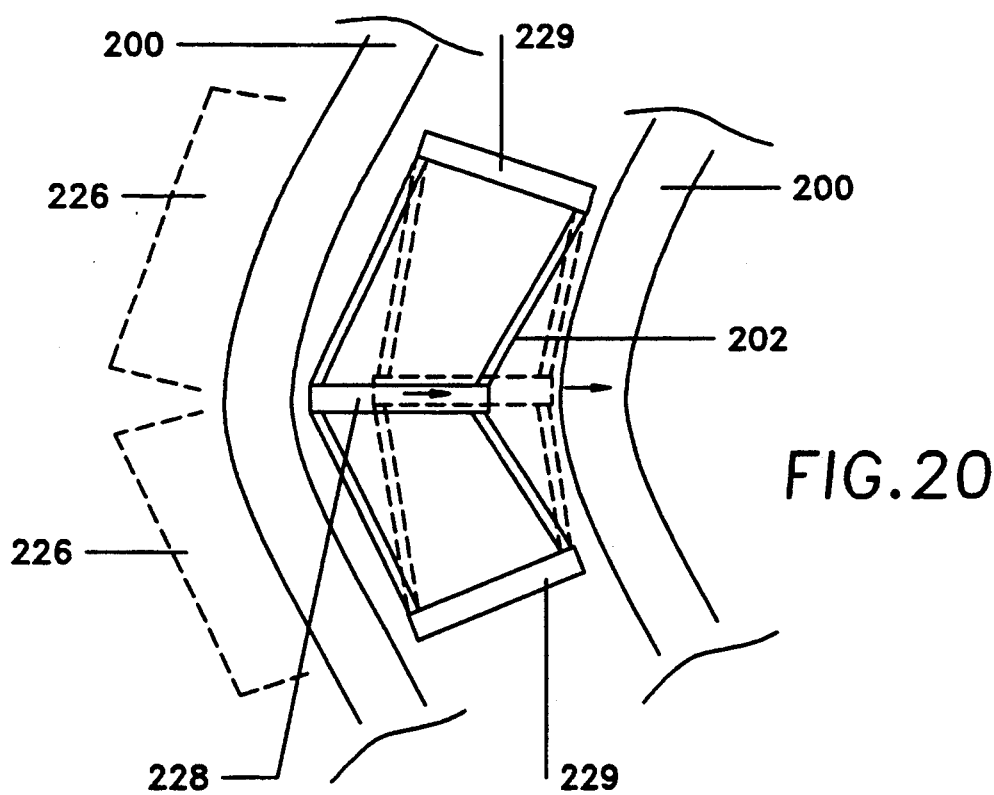
FIG. 20
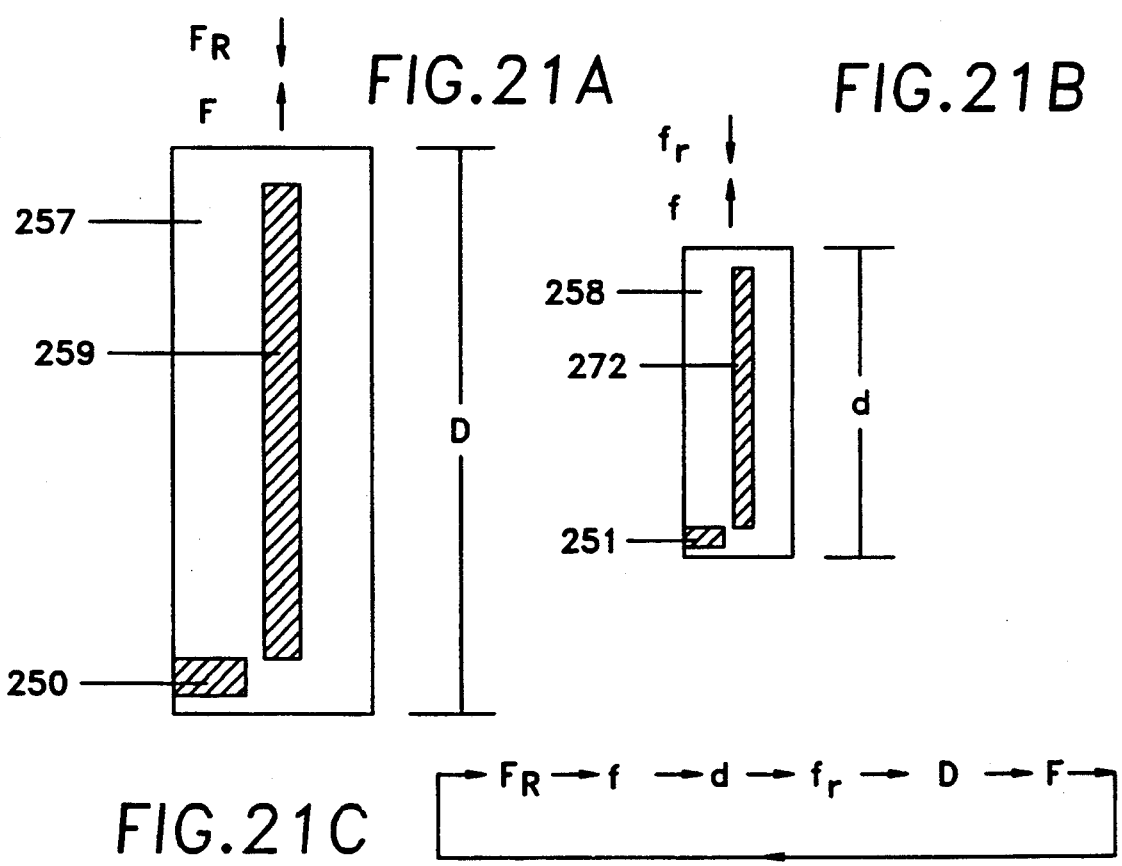
FIG. 21A  FIG. 21B
FIG. 21C

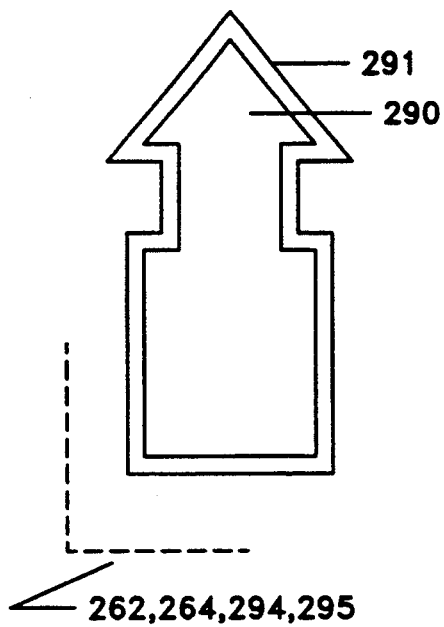
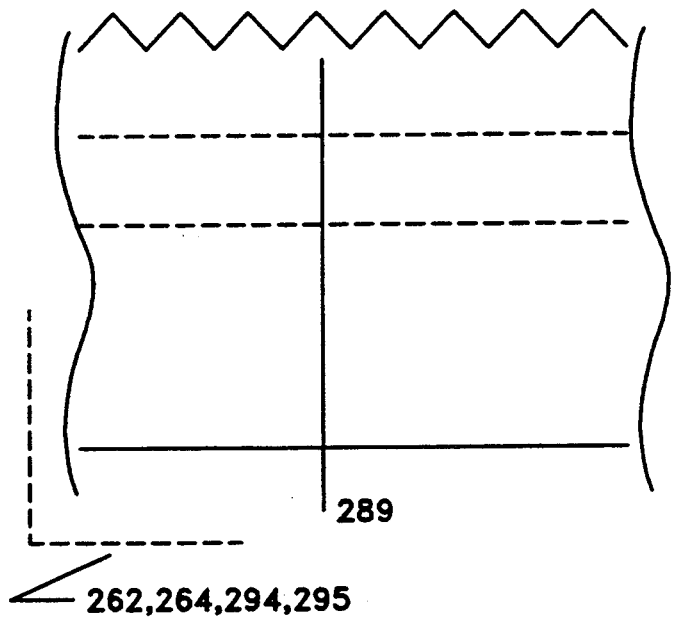
FIG.29  FIG.30
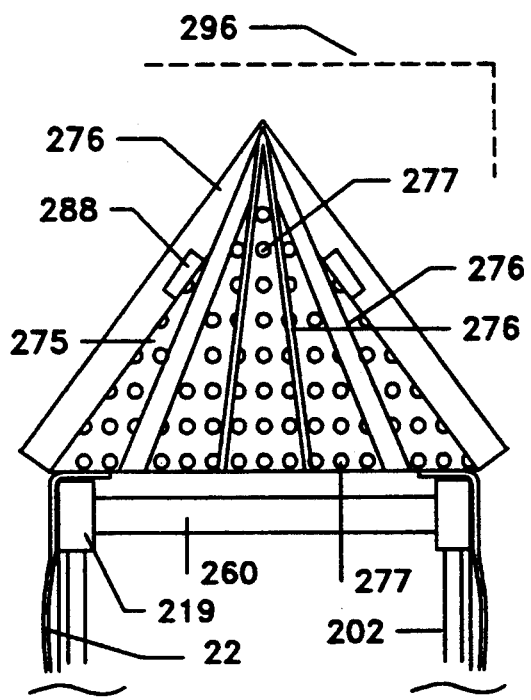
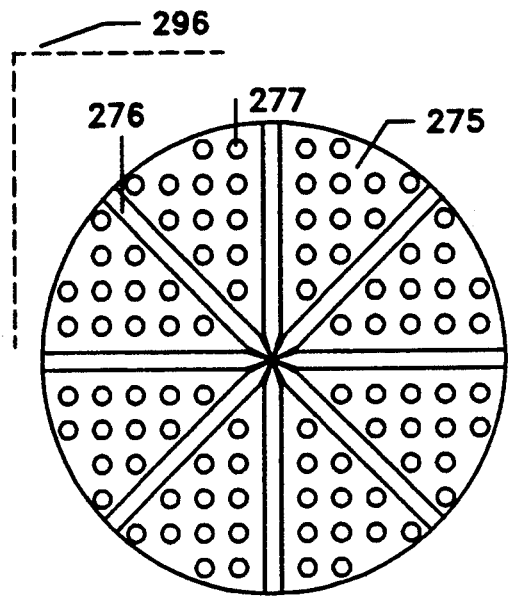
FIG.31  FIG.32

ROBOTIC SNAKE

BACKGROUND OF THE INVENTION

This invention reveals improvements in a flexible robotic limb which can function as a robotic snake, here called a robo-snake. These improvements are particularly pertinent to miniaturization applications such as catheters or positioners for microsurgery, micro-assembly, micro-manipulation, or micro-exploration. This invention features improvements in a prior-art flexible robotic arm of Rennex, U.S. Pat. No. 5,129,279, which issued in July, 1992. This prior-art invention incorporated the following basic structural features. The flexible arm comprised a series of expansible base units which were interconnected by six independently controlled length actuators. This interconnection was accomplished with universal joints. This structure was very versatile is terms of its motion. Each stage could extend, tilt, twist, and expand or contract radially. The combination of stages could position its working end along a tortuous path, and it could self-propel itself along a grid, a tunnel, or a blood vessel. It could also grip objects or position tools or imaging devices. Other features included optimal simplicity of control, ease of construction, lightness, and stiffness.

The most important element of the current invention in its two forms, a robo-snake or a flexible robotic arm, is the length actuators, especially for miniaturization. Inventor Rennex has submitted three patents for length actuators with the same application date as for the current invention. (These serial numbers will be provided.) All three of these attempt to minimize the actuator size. The first is titled "Inchworm Actuator"; it provides for improvements over the prior art of inchworm linear motors to achieve miniature actuators. The second is titled "Micro-Actuator"; it provides for a two-way, micro-machined actuator which can be internally locked at a particular length. The third is titled "Free-Standing Traveling-Wave Actuator"; it provides for a traveling-wave ultrasonic motor of minimal size which can be free-standing as required in the robo-snake. All of these actuators can be configured in such a way that they are "free-wheeling" when the power is cut off, which may be an advantage in terms of safety.

SUMMARY OF THE INVENTION

This invention extends the capabilities of the prior-art invention of Rennex to miniaturization applications by developing detailed new component designs and by combining it with systems for sensing, control, and signal transmission. These systems include pressure sensors, length sensors, protective skins, ultrasonic imagers, cutting tools, and multiplexing schemes.

A principle object of the present invention is to provide a flexible arm or snake which can assume shapes with considerable versatility and which can position its working end with high accuracy. A further object is to provide for a flexible snake which can self-propel itself through tunnels, tubes, or blood vessels and which can perform cleaning, sensing, cutting, and removal operations therein. A further object is to provide for a flexible snake which can remove plaque from the interior of blood vessels in a certain, precise, and immaculate manner, even for the most difficult cases in terms of blockage or tortuosity. A further object is to provide for a flexible snake which can tunnel through material such as living tissue along a versatile path, thereby avoiding particular obstacles.

BRIEF DESCRIPTION OF THE DRAWINGS

FIG. 2 is a side view of a prior art length actuator.

FIG. 3 is a perspective drawing of a prior art vertex of six length actuators and six universal joints.

FIG. 6A-D shows schematic side views of of a robotic snake demonstrating its means of self-propulsion, according to the first embodiment of the invention.

FIG. 7 shows a schematic side view of a robotic snake demonstrating a folding feature of its means of self-propulsion, according to the first embodiment of the invention.

FIG. 15 is a front cross-sectional view of a robotic snake showing sensor components, according to the first embodiment of the invention.

FIG. 16 is a top schematic view of an area-change section of a robotic snake showing curved base length actuators, according to the first embodiment of the invention.

FIG. 17 is a perspective view of an area-change section of a robotic snake showing monolithic pivots, according to the first embodiment of the invention.

FIG. 20 is a schematic side view of two stages of a robotic snake showing a control technique, according to the first embodiment of the invention.

FIG. 21A-C depicts elements of a tele-robotics system for a length actuator, according to the third embodiment of the invention.

FIG. 29 is a front view of a hot-wire variation of a cutting hoop of a robotic snake showing an insulating layer, according to the sixth embodiment of the invention.

FIG. 30 is a side view of a saw-tooth cutting hoop of a robotic snake, according to the sixth embodiment of the invention.

FIG. 31 is a profile side view of a penetration tool of a robotic snake, according to the seventh embodiment of the invention.

FIG. 32 is a top view of a penetration tool of a robotic snake, according to the seventh embodiment of the invention.

DESCRIPTION

This invention extends the capabilities of the prior-art invention of Rennex to miniaturization applications by developing detailed new designs for the length actuators and the universal joints. The first 5 figures and the descriptive text are taken from said prior art U.S. Pat. No. 5,129,279 of Rennex.

Figure 1:
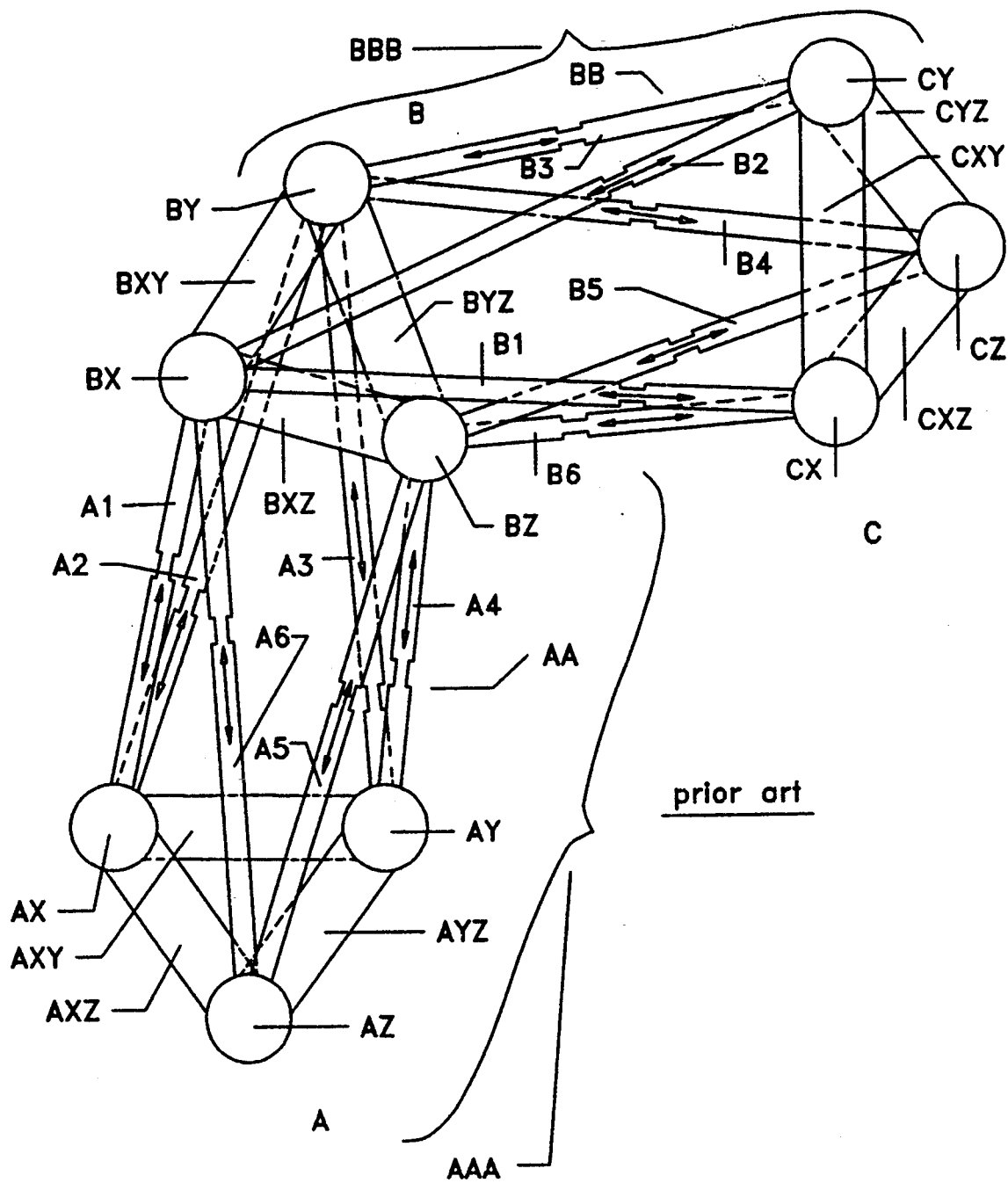
FIG. 1 is a perspective drawing of a prior art flexible robotic limb, showing two articulation units.

FIG. 1, a perspective drawing of said prior art flexible robotic limb, shows two articulation units, a second articulation unit, BBB, and a first articulation unit, AAA, for the flexible limb. Here, a single letter—A,B, or C—refers to a base section or a fore section, a double letter—AA or BB—refers to a lengthwise interconnect, and a triple letter—AAA or BBB refers to an articulation unit. Each articulation unit consists of a base section, a lengthwise interconnect, and a fore section. That is, first articulation unit AAA consists of first unit base section A, first unit fore section B, and first unit length section AA. In turn, first unit base section A consists of first unit vertex AX which is connected by first unit connective element AXY to first unit vertex AY, which is connected by first unit connective element AYZ to first unit vertex AZ, which is connected by first unit connective element AXZ to first unit vertex AX. And, first unit fore section B consists of first unit vertex BX which is connected by first unit connective element BXY to first unit vertex BY, which is connected by first unit connective element BYZ to first unit vertex BZ, which is connected by first unit connective element BXZ to first unit vertex BX.

Also, first unit length section AA comprises first unit first actuator length element A1 and first unit second actuator length element A2, each of which is rotatably connected to first unit vertex AX. First unit length section AA further comprises first unit third actuator length element A3 and first unit fourth actuator length element A4, each of which is rotatably connected to first unit vertex AY. First unit length section AA further comprises first unit fifth actuator length element A5 and first unit sixth actuator length element A6, each of which is rotatably connected to first unit vertex AZ. Also, for the interconnections with first fore section B, first unit first actuator length element A1 and first unit sixth actuator length element A6 are rotatably connected to first unit vertex BX. First unit second actuator length element A2 and first unit third actuator length element A3 are rotatably connected to first unit vertex BY. And, first unit fourth actuator length element A4 and first unit fifth actuator length element A5 are rotatably connected to first unit vertex BZ.

Continuing the example of FIG. 1, second articulation unit BBB consists of second unit base section B, second unit fore section C, and second unit length section BB. In turn, second unit base section B consists of second unit vertex BX which is connected by second unit connective element BXY to second unit vertex BY, which is connected by second unit connective element BYZ to second unit vertex BZ, which is connected by second unit connective element BXZ to second unit vertex BX. And, second unit fore section C consists of second unit vertex CX which is connected by second unit connective element CXY to second unit vertex CY, which is connected by second unit connective element CYZ to second unit vertex CZ, which is connected by second unit connective element CXZ to second unit vertex CX.

Also, second unit length section BB comprises second unit first actuator length element B1 and second unit second actuator length element B2, each of which is rotatably connected to second unit vertex BX. Second unit length section BB further comprises second unit third actuator length element B3 and second unit fourth actuator length element B4, each of which is rotatably connected to second unit vertex BY. Second unit length section BB further comprises second unit fifth actuator length element B5 and second unit sixth actuator length element B6, each of which is rotatably connected to second unit vertex BZ.

Also, for the interconnections with second fore section C, second unit first actuator length element B1 and second unit sixth actuator length element B6 are rotatably connected to second unit vertex CX. Second unit second actuator length element B2 and second unit third actuator length element B3 are rotatably connected to second unit vertex CY. And, second unit fourth actuator length element B4 and second unit fifth actuator length element B5 are rotatably connected to second unit vertex CZ.

As can be seen, first unit fore section B is, in fact, second unit base section B. That is, each articulation unit shares a base section and/or a fore section with its neighboring articulation units. Also, the two articulation units in FIG. 1 may be extended to any number of like articulation units.

FIG. 2 depicts a prior art standard actuator length element 1, which is typical of those shown in FIG. 1 as A1-A6 and B1-B6. These sets of six standard actuator lengths comprise a length section such as first unit length section AA. Standard actuator length element 1 comprises upper female threaded rod 2, which is hollow and which is rigidly attached to actuator motor 12, located inside the upper section of upper female threaded rod 2. Actuator motor 12 with electrical leads 5 causes motor shaft 10 to rotate. When power to the motor stops, the actuator retains its current length with no further power requirement. The top half of male double threaded rod 4 is normally threaded and screws into upper female threaded rod 2 by clockwise rotation; the bottom half of male double threaded rod 4 is reverse threaded and screws into lower female reverse threaded rod 6 (also hollow) by the same clockwise rotation. Thus, this clockwise rotation shortens standard actuator length element 1, and, similarly, counterclockwise rotation lengthens standard actuator length element 1.

The just-mentioned rotation is achieved due to the rigid attachment of motor shaft 10 to the top of male double threaded rod 4 via end plate 8.

FIG. 3 shows a typical prior art vertex of a base section such as second unit first vertex BX of FIG. 1. In the first embodiment of the prior art invention, second unit first connective element BXY and second unit second connective element BXZ are fixed-length rods, optionally hollow, which are rigidly attached to joint plate 17. The following are rotatably attached to joint plate 17, via universal joints 15 and pins 13: on its top side, first unit first actuator length element A1 and first unit sixth actuator length element A6, and on its bottom side, second unit first actuator length element B1 and second unit second actuator length element B2.

FIG. 3 is a perspective drawing of a prior art vertex of six length actuators and six universal joints; it shows prior art universal joints which interconnect actuator length elements such as A1 with a base or fore section. Looking at FIGS. 1 and 3, note that a taper feature can be achieved in the following way. The lengths of connective elements in a base or fore section, such as second unit connective element BXY, can be varied from articulation unit to articulation unit, along the length of the flexible limb. Also, to achieve branching, it would be a simple matter for those skilled in the art to attach a plurality of separate flexible limbs either to the side of the flexible limb or to its end, via the base section shown in FIGS. 1 and 3.

Figure 4:
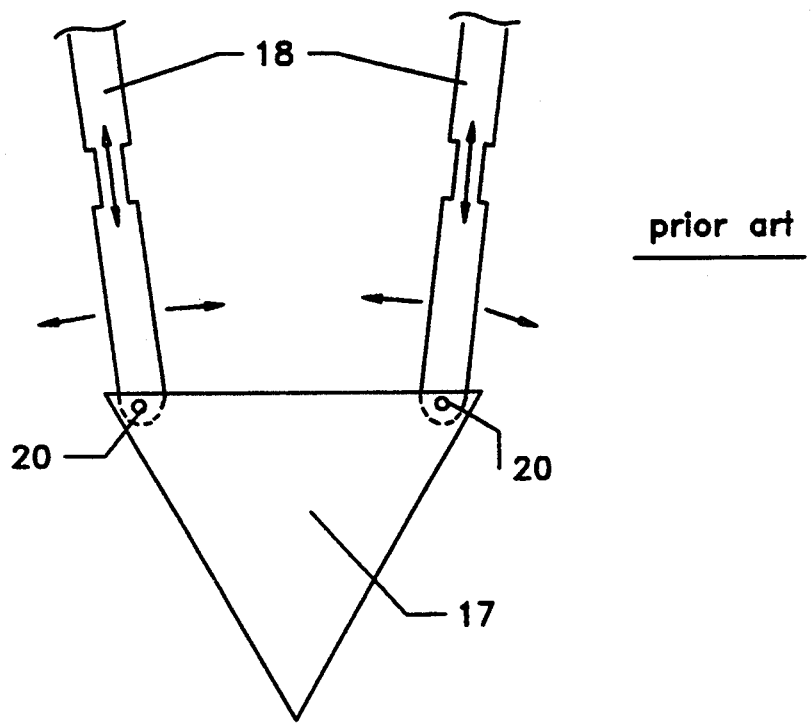
FIG. 4 is a top view of a prior art unit base element or area-change section showing pivots for base length actuators.

FIG. 4 is a top view of a prior art unit base section, also called an area-change section, showing pivots 20 for base length actuators 18. This feature is necessary to change the cross-sectional area of a unit base section. That is, an actuator length element is used for a base connective element, such as second unit base connective element BXY shown in FIG. 1. This replacement requires that base length actuators 18 be free to rotate in the plane of the base section, that is, the plane of joint plate 17. This rotation is achieved via base pivots 20 which connect base length actuators 18 to base plate 17.

One advantage of the just-mentioned embodiment of the invention is that it has the ability to either squeeze an object located inside the flexible limb or to expand within a hole into which the flexible limb has been inserted. This advantage leads to anchorage and gripping capabilities. Another advantage is that the cross-sectional area can be reduced to allow access into or through small openings. For example, it is possible to achieve a taper feature in which the cross-sectional area progressively decreases along the length of the flexible limb. It should also be understood that greater versatility in terms of strength and gripping can be achieved by using a multiplicity of flexible arms. In addition, a branching feature can be easily utilized in which a multiplicity of smaller flexible limbs branch out from a trunk flexible limb, and this branching can occur more than once.

Figure 5:
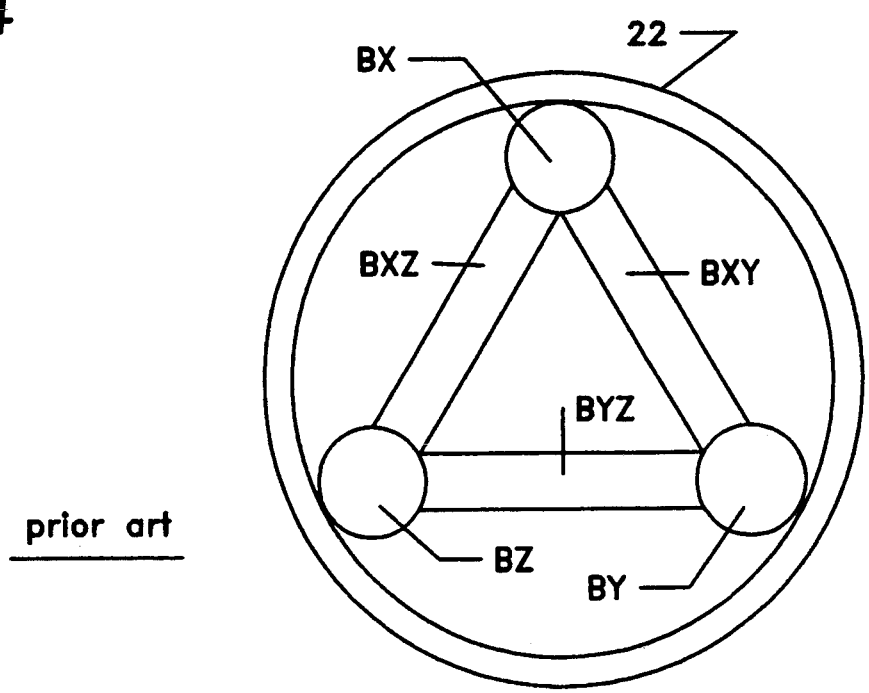
FIG. 5 is a side view of a prior art base unit or area-change section showing an outer skin.

FIG. 5 shows a cross-section of the flexible robotic limb with outer elastic skin 22, which extends around second unit base section B and along the length of the flexible limb, serving to protect the inner mechanisms of the invention and to aid gripping capability as the flexible limb wraps around an object. Outer elastic skin 22 could be composed of metallic, cloth, plastic or synthetic material, in solid or mesh from.

It should be understood that the prior art flexible robotic limb just described and the improved flexible robotic limb of this patent could also function as a robotic snake. The distinction between these two functions is the following. A flexible robotic limb would be anchored at one end to a fixed location or, perhaps, a moving location. A robotic snake could move across a grid or through a blood vessel or and existing tunnel, it could bore its way through a medium thereby creating a tunnel, or it could bore its way through a blocked blood vessel. In addition, a robotic snake could anchor itself by radial expansion within a blood vessel, or it could anchor itself to a guide wire which would also pass through a tunnel or blood vessel. The first embodiment of the invention is of a robotic snake, but many of its features could be applied to a flexible robotic limb.

FIG. 6A-D shows a schematic side view of robotic snake 225 demonstrating its means of self-propulsion, according to the first embodiment of the invention. The terminology to describe the this invention is the following. A stage is equivalent to one of the articulation units, e.g. AAA or BBB, in FIG. 1. Each stage 226 comprises a length-change section 202 and two area-change sections 201, one on either end of length-change section 202. The two area-change sections 201 of FIG. 6 correspond to the base section and the fore section of FIG. 1, and the length-change section of FIG. 6 corresponds to the lengthwise interconnect of FIG. 1. FIGS. 6-A, B, and C depict 3 time stages in the self propulsion of robotic snake 225. For clarity in this discussion of self-propulsion, the terms expansion and contraction will refer to radial motion, and the terms lengthen and shorten will refer to lengthwise motion along the tunnel. Finally, the representation of length-change sections is two-dimensional. It should be understood the actual motion of robotic snake 225 is three-dimensional.

In time stage of FIG. 6A, the rearward stage, on the left and located at position 203, has one or more area-change sections 201 in an expanded state to anchor within tunnel walls 200. At the same time, the area-change sections of the stages 226 located in both the center region the forward region are contracted, for easy passage through tunnel walls 200. Also, the length-change sections 202 of the center stages 226 are shortened.

Time stage of FIG. 6B shows that the length-change sections 202 of the center stages 226 have lengthened, and the front end of robotic snake 225 has moved from position 204 to position 206. Time stage of FIG. 6C shows that the area-change sections 201 of the forward stages 226 have expanded to anchor within tunnel walls 200, the area-change sections 201 of the rearward stages 226 have contracted, and the length-change sections 202 of the center stages 226 have shortened, thereby pulling the rearward stages 226 to position 205.

Repetition of the above sequence results in self propulsion of robotic snake 225 in a forward direction through tunnels walls 200, and self propulsion in the rearward direction can be achieved in an equivalent and obvious manner.

It should be understood that a similar method of propulsion can be used to enhance the method just discussed or as a separate method in and of itself. This method is depicted in FIG. 6D; it utilizes bends in robotic snake 225, at either end, to achieve anchoring against tunnel walls 200. This method can also be used to significantly increase the maximum size of tunnel walls 200 inside of which self-propulsion can be achieved.

FIG. 7 shows a schematic side view of robotic snake 225, demonstrating a folding feature of its means of self-propulsion, according to the first embodiment of the invention. The area-change sections 201 of the center stages 226 have been tilted to present a smaller area cross-section, "ww" than that indicated by "w" of stage 226 at the end of robotic snake 225. This allows passage through smaller tunnel walls 200, especially if these tunnel walls 200 are resilient, as is the case for blood vessels.

Figures 8, 9A, 9B:
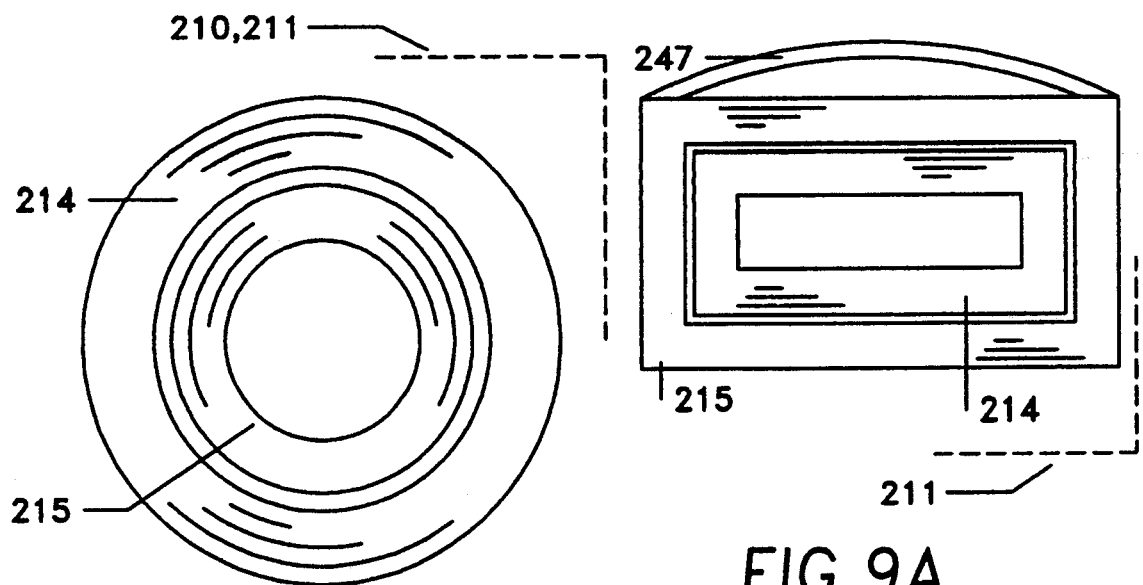
FIG. 8 is a simplified version of a length actuator of a robotic snake showing its telescopic nature, according to the first embodiment of the invention.
FIG. 9A-B shows two versions of a top cross-sectional view of an asymmetric length actuator of a robotic snake, according to the first embodiment of the invention.

FIG. 8 is a simplified version of a length actuator 211 of robotic snake 225, showing its telescopic nature, according to the first embodiment of the invention. Outer telescopic element 214 slides past inner telescopic element 215 for actuation. Various actuators which drive this telescopic action will be described later. Remember that length-change section 202 is comprised of six length actuators 211. In FIG. 8, a cylindrical geometry happens to be employed. In FIG. 9A-B, a top cross-sectional view of an asymmetric length actuator of a robotic snake, according to the first embodiment of the invention, two other geometries are employed. In FIG. 9A, a rectangular geometry is employed, with length cladding 247 which is attached to outer telescopic element 214 to provide better contact with a surrounding tunnel wall 200, when radial expansion is employed for self propulsion. In FIG. 9B, a curved geometry is employed.

Figure 10:
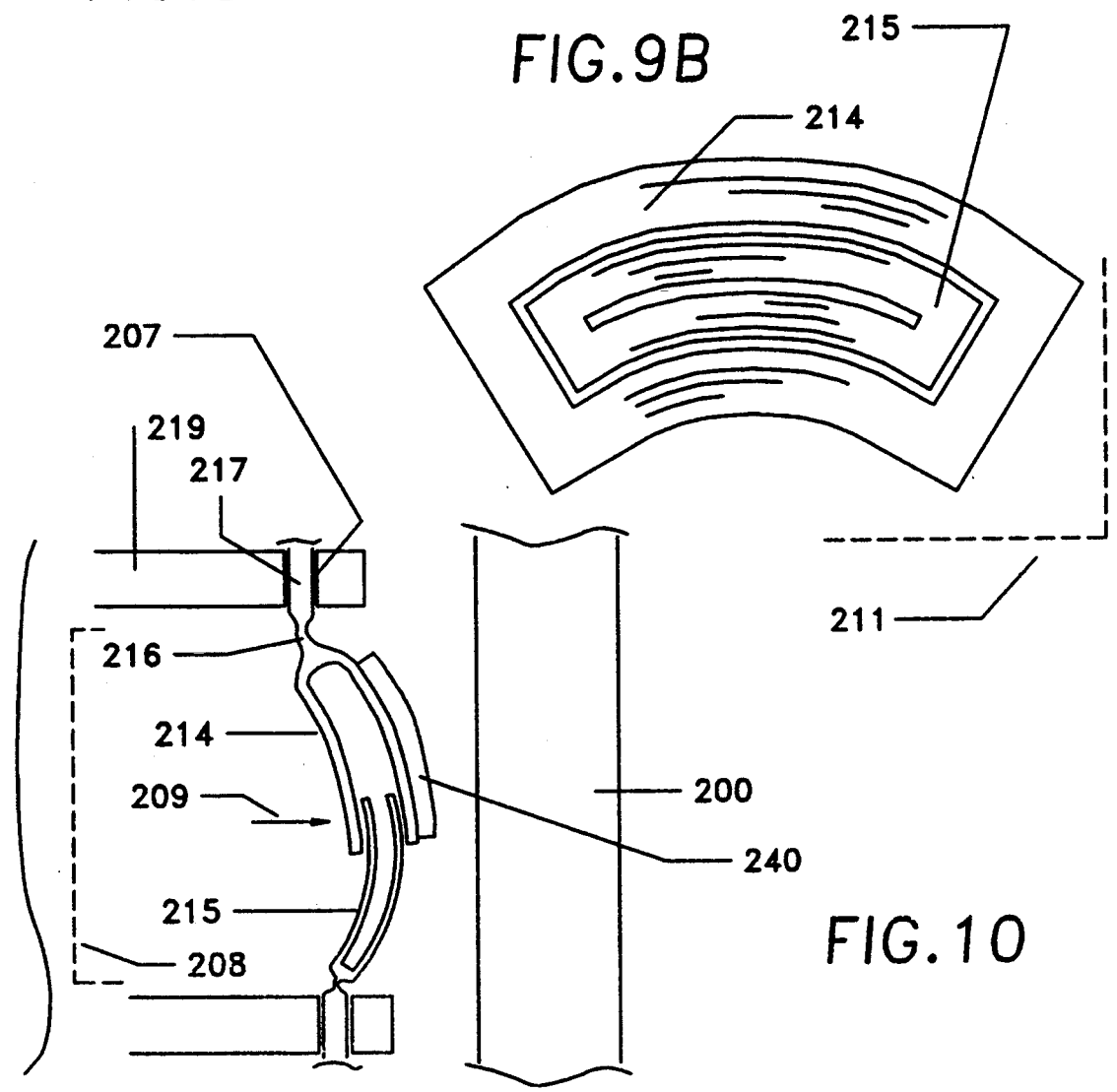
FIG. 10 is a side view 6f a simplified version of a length actuator and universal joint of a robotic snake, according to the first embodiment of the invention.

FIG. 10 is a side view of a schematic version of length actuator 211, shown here as bowed length actuator 208, and universal neck 216 which is a type of universal joint for a robotic snake, according to the first embodiment of the invention. For miniature applications the structure, comprising neck end 217, universal neck 216 and either outer telescopic element 214 or inner telescopic element 215, may be monolithically machined. Alternatively, universal neck 216 could be made separately from outer or inner telescopic element 214 or 215 which would allow different materials to be optimally used for the two different functions of these two components. The material should be resilient so as to not break after many bending actions. In place of bowed length actuator 208, one could optionally use a straight length actuator 211 as shown in FIG. 11.

In FIG. 10, bowed length actuator 208 is bowed toward the exterior, for greater expansion force capability. As outer telescopic element pushes outward in the direction of arrow 209 against tunnel wall 200, pressure sensor 240, located on the exterior of outer telescopic element 214, senses the expansion pressure. This parameter is needed for various control methods to be discussed later. Universal neck 216 widens to neck end 217 which is fixedly attached to base corner 219 via base hole 207. The two adjoining neck ends 217 in a particular base hole 207 might also be monolithically machined.

Figure 11:
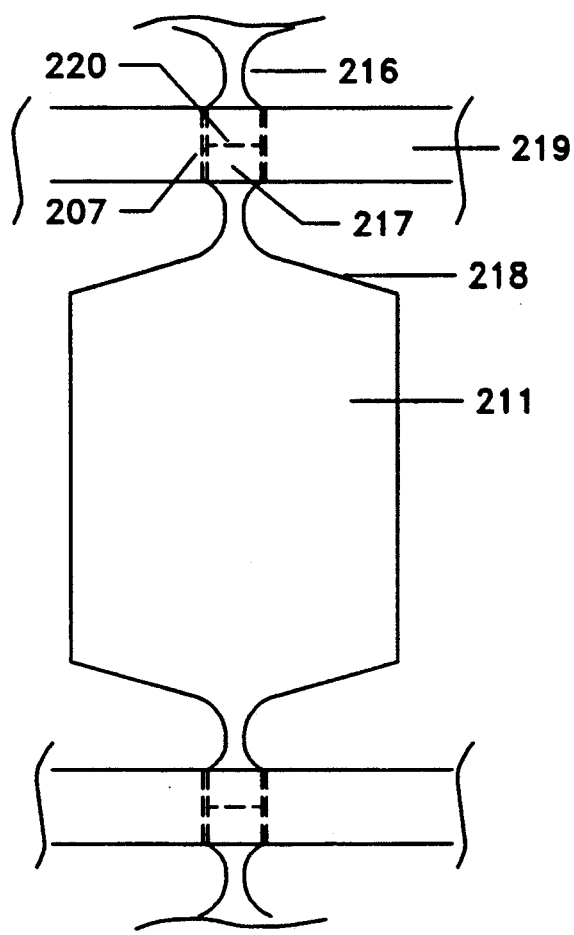
FIG. 11 is a profile front view of an asymmetric length actuator of a robotic snake showing a monolithic-hinge universal joint, according to the first embodiment of the invention.

FIG. 11 is a profile front view of an asymmetric length actuator 211 of robotic snake 225 showing a universal neck 216 version of a universal joint, according to the first embodiment of the invention. It shows optional break 220, indicating that the two neck ends 217 from either side may not be monolithic. The asymmetry, that is the fact that the width of length actuator 211 is greater than the thickness, allows for a better contact when anchoring of length actuator 211 against tunnel wall 200—when the adjoining area-change sections are radially expanded against tunnel wall 200. Another advantage of this asymmetry is that the cross-sectional area needed for actuation is distributed around the perimeter of robotic snake 225, thereby allowing a greater lumen within hollow robotic snake 225 than if length actuators 211 were cylindrical.

Figure 12:
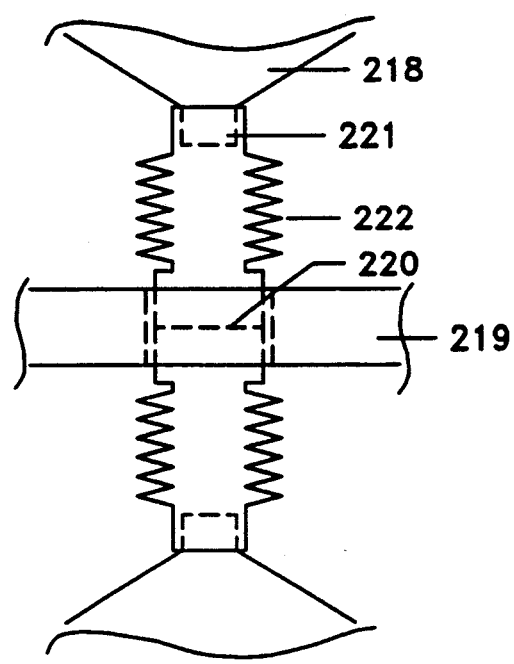
FIG. 12 is a profile front view of a bellows universal joint of a robotic snake, according to the first embodiment of the invention.
Figure 13:
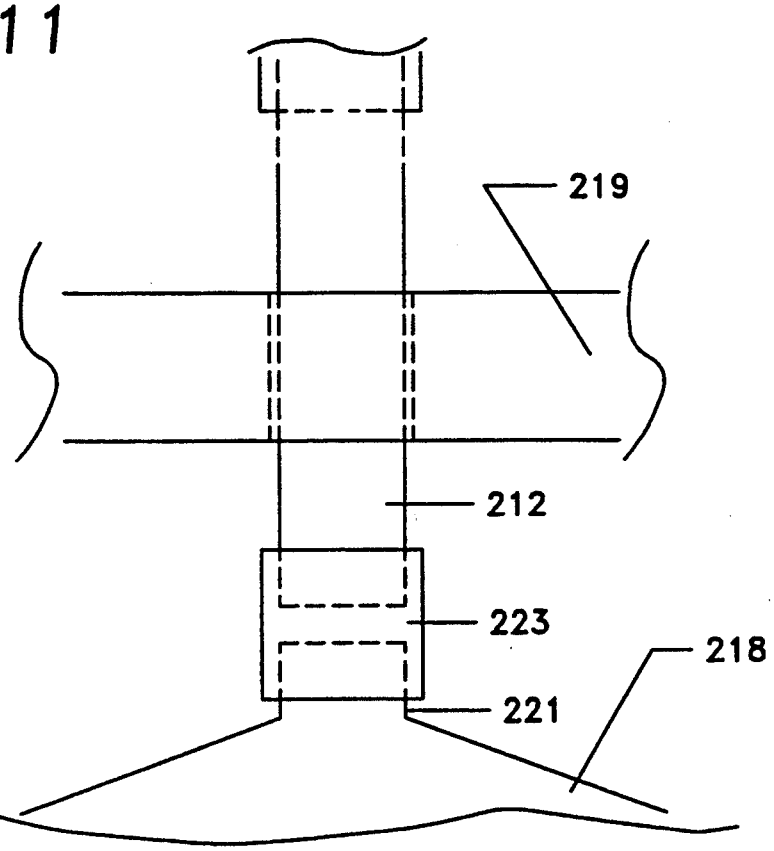
FIG. 13 is a profile front view of flexible tubing universal joint of a robotic snake, according to the first embodiment of the invention.

FIG. 12 is a profile front view of bellows universal joint 222 of robotic snake 225, according to the first embodiment of the invention. Bellows universal joint 222 is fixedly attached, on one end, to cap end 221 of universal cap 218 which forms the end of outer or inner telescopic elements 214 or 215 and, on the other end, to base corner 219. FIG. 13 is a profile front view of flexible tubing universal joint 223 of robotic snake 225, according to the first embodiment of the invention. Flexible tubing universal joint 223 connects cap end 221 with base post 212.

Figure 14:
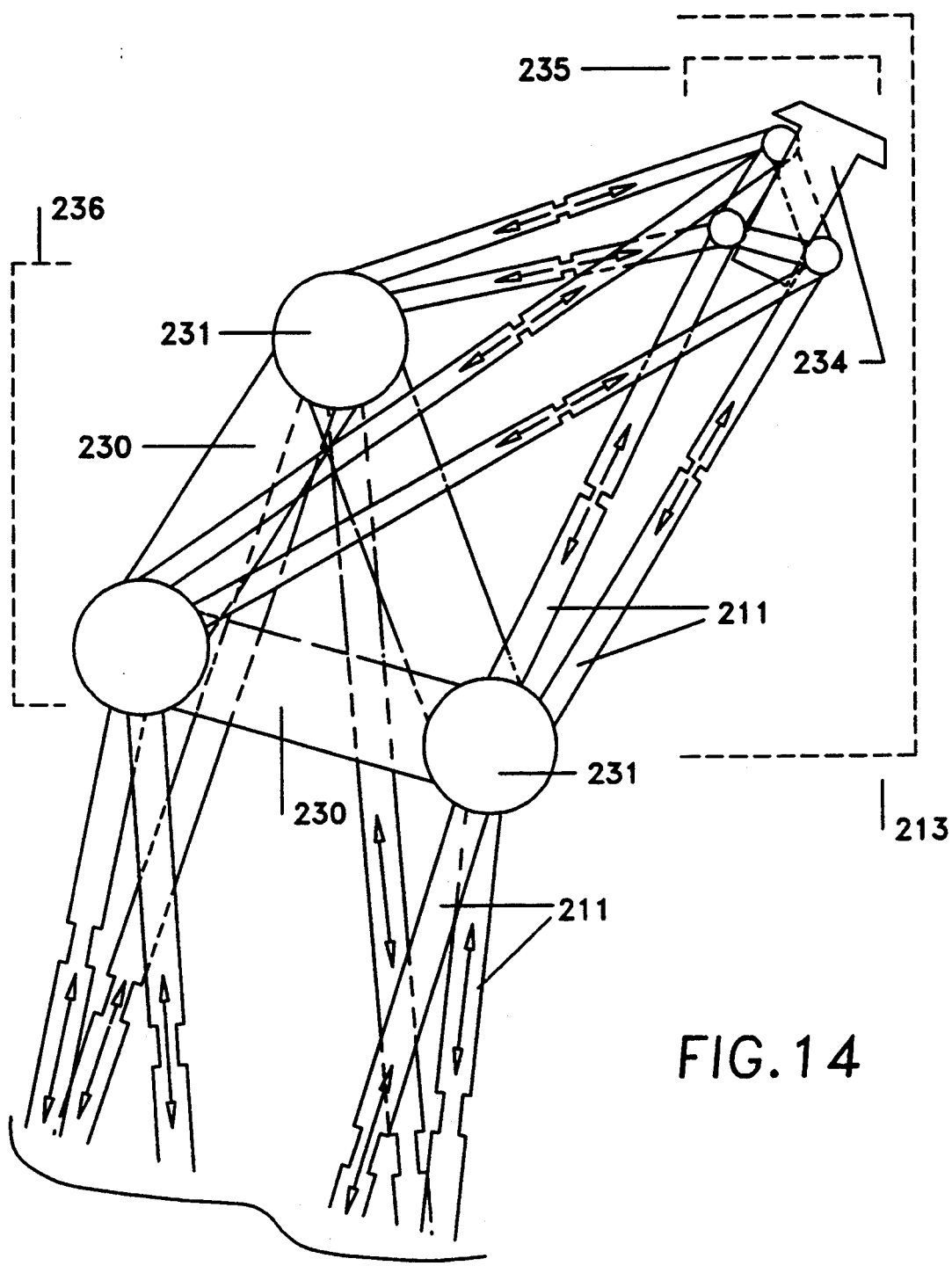
FIG. 14 is a perspective view of a working end of a robotic snake, according to the second embodiment of the invention.

FIG. 14 is a perspective view of working end 213 of robotic snake 225, according to the second embodiment of the invention. It is distinguished from the previous embodiment in that the final fore section, namely tool base 235 is smaller than the final base section, namely base 236. This allows a more precise cutting capability in terms of precision location and tilting range for generic cutter 234 which is held by tool base 235. Again, the positioning of generic cutter 234 is accomplished by activating length actuators 211. Tools other than a cutter could also be positioned such as an imager or a laser. Also, this arrangement with generic cutter 234 on working end 213 could be used to bore a tunnel. Finally, the size of generic cutter 234 could range from much smaller to larger than the size of base 236, depending on the application.

FIG. 15 is a front cross-sectional view of robotic snake 225 showing sensor components, according to the first embodiment of the invention. Again, note that the actual actuating element that drives outer telescopic element with respect to inner telescopic element 215 is not shown. FIG. 15 is similar to FIG. 11 except for the addition of sensors to measure actuator length and external pressures (or forces). Length sensor 241 measures the length of length actuator 211. Axial pressure sensor 243, located in pressure slot 242, measures the axial force on length actuator 211.

An additional feature is elastic skin 237, made of an elastic material such as latex; this surrounds outer and inner telescopic elements 214 and 215 to protect them from the environment. Elastic skin 237 is attached to the upper portion of outer telescopic element 214 or the lower portion of inner telescopic element 215 via skin clamps 239 which seal elastic skin 237 against skin notches 238 in outer or inner telescopic elements 214 or 215.

FIG. 16 is a top schematic view of area-change section 201 of robotic snake 225 showing curved base length actuators 245, according to the first embodiment of the invention. It should be understood that the base length actuators could be straight as well. Curved base length actuators 245 are curved to ensure the maximum contact of the exterior of the area-change section 201 with the surrounding tunnel walls 200.

Other features shown in FIG. 16 include pressure sensors 240 located on the exterior of outer telescopic elements 214 to measure radial forces and perimeter imaging elements 254 located on the inward sides of outer telescopic elements 214 for imaging of the environment surrounding robo-snake 225. Also shown here and in FIG. 17 are monolithic pivots 224 for interconnection of outer or inner telescopic elements 214 or 215 with base corners 219, with base holes 207 for attachment with length actuators 211.

Figure 18:
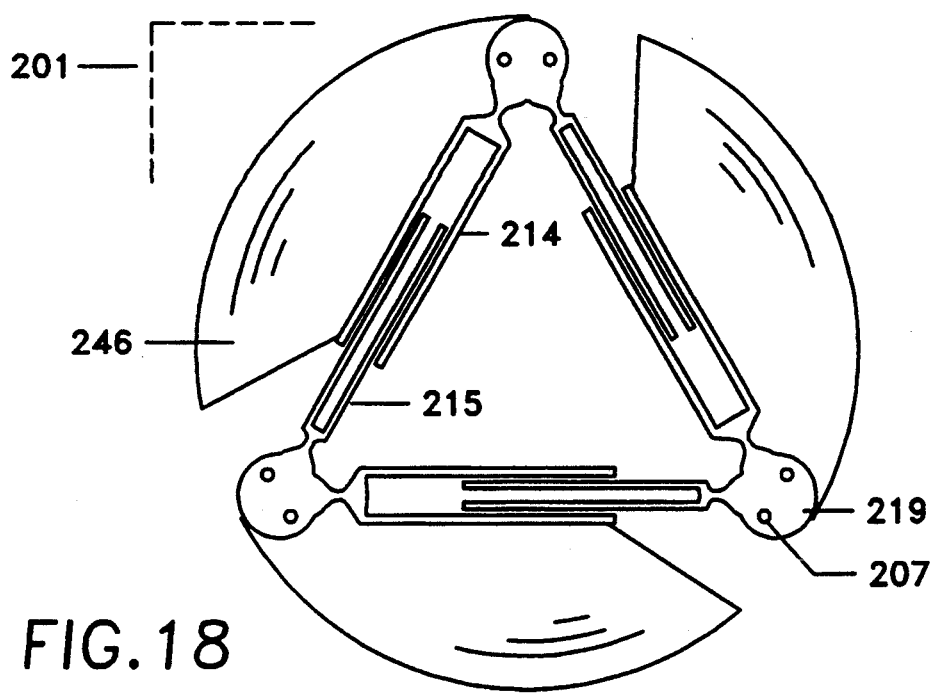
FIG. 18 is a schematic top view of an area-change of a robotic snake showing base cladding according to the first embodiment of the invention.

FIG. 18 is a schematic top view of area-change section 201 of robotic snake 225 showing base cladding 246 which is attached to outer telescopic element 214.

Figure 19:
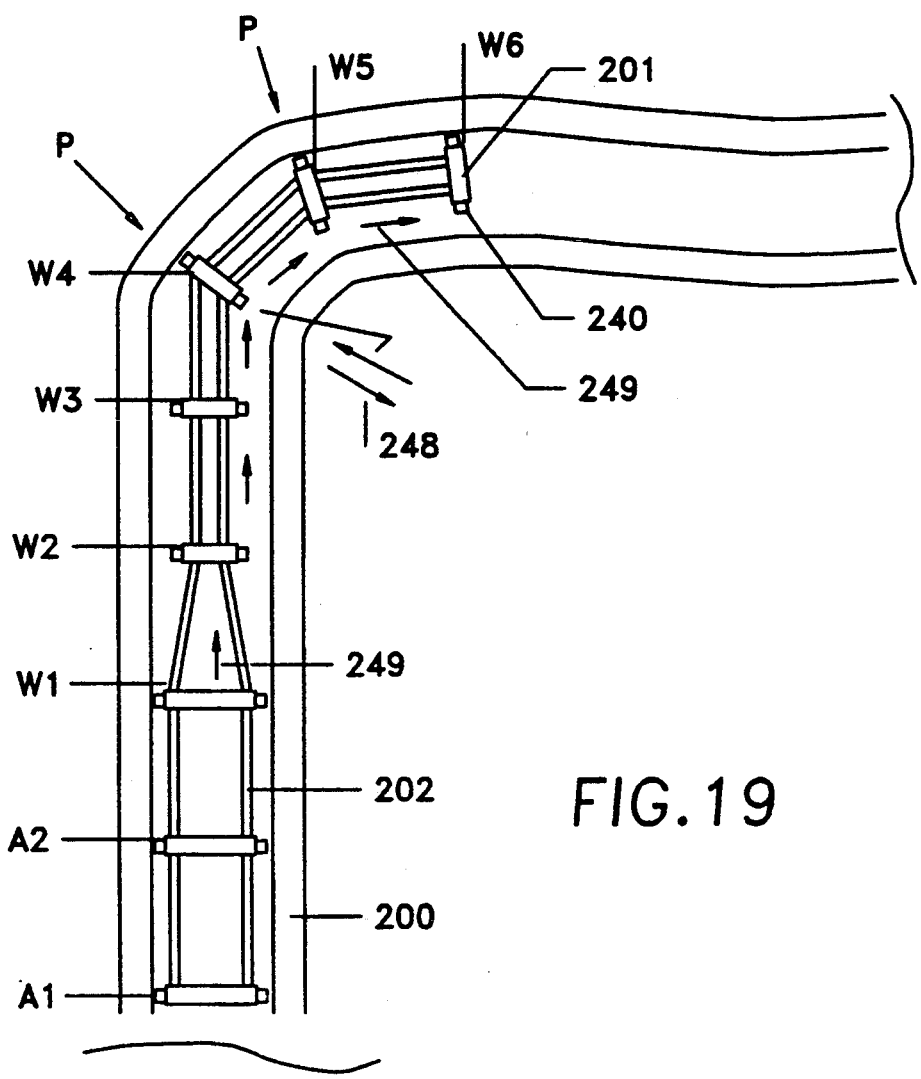
FIG. 19 is a schematic side view of a robotic snake in a tunnel or blood vessel showing anchor and working stages, according to the first embodiment of the invention.

FIG. 19 is a schematic side view of robotic snake 225 in a tunnel or blood vessel showing anchor stages A{i} and working stages W{i}, according to the first embodiment of the invention. The general control strategy is to allow robotic snake 225 to self-propel along tunnel walls 200 with a minimum of force being exerted against tunnel walls 200. It is important to realize the robotic snake is a rigid structure which actively changes its shape; it is not a pliable structure which will automatically bend to prevent damage to tunnel walls 200. The advantage of this rigidity is a capability for precise location and a capability to push hard through obstructions. The danger of this changeable rigidity is that a part of robotic snake 225 might be forcefully pushed in the wrong direction so as damage tunnel walls 200. When the actuating elements are discussed later in this patent, a free-wheeling mode of operation will be mentioned; this allows a robotic snake to function as a passive and pliable device.

Referring to FIG. 19 and to FIG. 20, which is a schematic side view of two stages of robotic snake 225 showing a control technique, according to the first embodiment of the invention, the following strategy can be used to control robotic snake 225 to move along tunnel walls 200 with a minimum of force exerted by robotic snake 225 against tunnel walls 200. Assume that robotic snake 225 is in a longitudinally shortened state at a particular location within tunnel walls 200. Let us define two trajectories: the 3-dimensional tunnel trajectory, Tw, is defined by the locus of center points of tunnel walls 200 and the 3-dimensional robotic snake trajectory, Ts, is defined by the locus of center points of robotic snake 225. The control goal is to match Ts to Tw as well as possible as the self propulsion takes place.

Tw can be discovered by the following interrogation. FIG. 20 shows that, for any pair of stages 226, center area-change section 228 can be moved laterally as indicated by arrows 248 and by the stages 226 in phantom, in such a manner that the two adjoining area-change sections 229 do not move. By three or more such interrogations, the locations of the surrounding tunnel walls 200 can be determined, and center area-change section 228 can be positioned so that its center point is aligned with Tw.

This interrogation can proceed along the entire length of robotic snake 225; the simplification is that it can be accomplished, one area-change section 201 at a time. Note, for an end area-change section, there is only one adjoining area-change section 229. After the interrogation, the length-change sections 202 of the working stages W{i} are changed to move according to arrows 249 in such a manner that Ts ia aligned with Tw. For the front end of robotic snake 225 Tw is not known, so the lateral interrogation of the front-most area-change section 201 must be repeated as the extension is occurring, to discover the newly probed portions of Tw.

Once the extension is completed, the rear end of robo-snake 225 is moved forward as was previously discussed for FIG. 6. In this way, the various stages 226 are self propelled along Tw. Note that this control strategy does not require an imaging system. In fact, the following mapping process might be accomplished in some cases, without an imaging system. Suppose that robotic snake 225 has self-propelled through a region of partial blockage in a blood vessel. It may be possible to utilize the information on Tw on either side of the blockage to estimate Tw, by interpolation, in the region of blockage, even if the lumen there is off center. Finally, remember that each length-change section 202 comprises six length actuators 211.

FIG. 21A–C depicts elements of a tele-robotics control system for length actuator 211, according to the third embodiment of the invention. Tele-robotic control refers to a system where there is a master component (FIG. 21A) and a slave component (FIG. 21B). Whatever the master component does is mimicked by the slave component. This requires a sensing system to measure the positions and forces of both the master and slave components, as well as communication systems and software control systems to transmit the necessary information back and forth between the master system and the slave system. Master length actuator 257 incorporates master pressure sensor 250 and master length sensor 259; slave length actuator 258 incorporates slave pressure sensor 251 and slave length sensor 272.

Tele-robotic control is achieved as follows. A force $F_R$, measured by master pressure sensor 250, is exerted by a person, e.g., on master length actuator 257 causing its length, D, measured by master pressure sensor 250, to change. At this time, slave length actuator 258 moves to allow its length, d, as measured by slave length sensor 251, to change. This may cause a reaction force $f_r$, by the slave environment on slave actuator 258, and this reaction force is equal the slave actuator force f measured by slave pressure sensor 251. The reaction force $f_r$ will cause d to change more slowly or not at all. In-this case, D will also not change, and the person exerting $F_R$ on master length actuator 257 will experience a different force F caused by action of master length actuator 257 as it attempts to match changes in D to changes in d.

Figure 22:
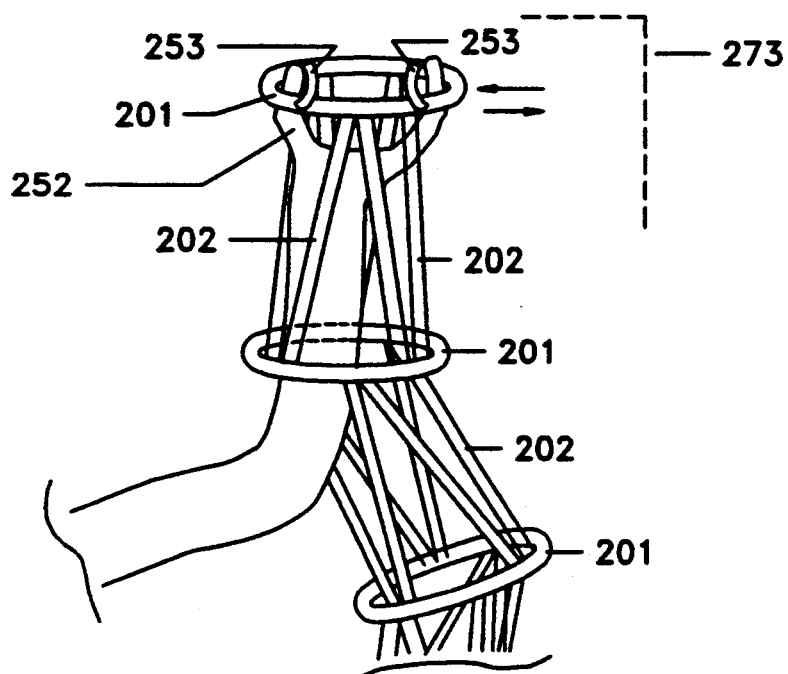
FIG. 22 is a perspective view of a master robotic snake, according to the third embodiment of the invention.

This interactive control is indicated in the loop of FIG. 21C. In a real application the master device would be an entire robot, and the slave device would be a miniature replica of the master robot. The control system described above would allow a person manipulating a master robot to sense resistance of a slave robot's motion by its surroundings. For example, FIG. 22 is a perspective view of master robotic snake 273, according to the third embodiment of the invention. A master's hand 252 is attached to master robotic snake 273 with finger straps 253. By opening or closing his fingers, a master's hand could control the radial expansion of the end area-change section 201 of master robotic snake 273. By tilting and moving, master's hand 252 could control the position of the end area-change section 201 of master robotic snake 273. At the same time, any resistance to these movements could be sensed by master's hand 252. Presumably, a person would be viewing a visual representation of an imaging system as she manipulates master robotic snake 273.

Figure 23:
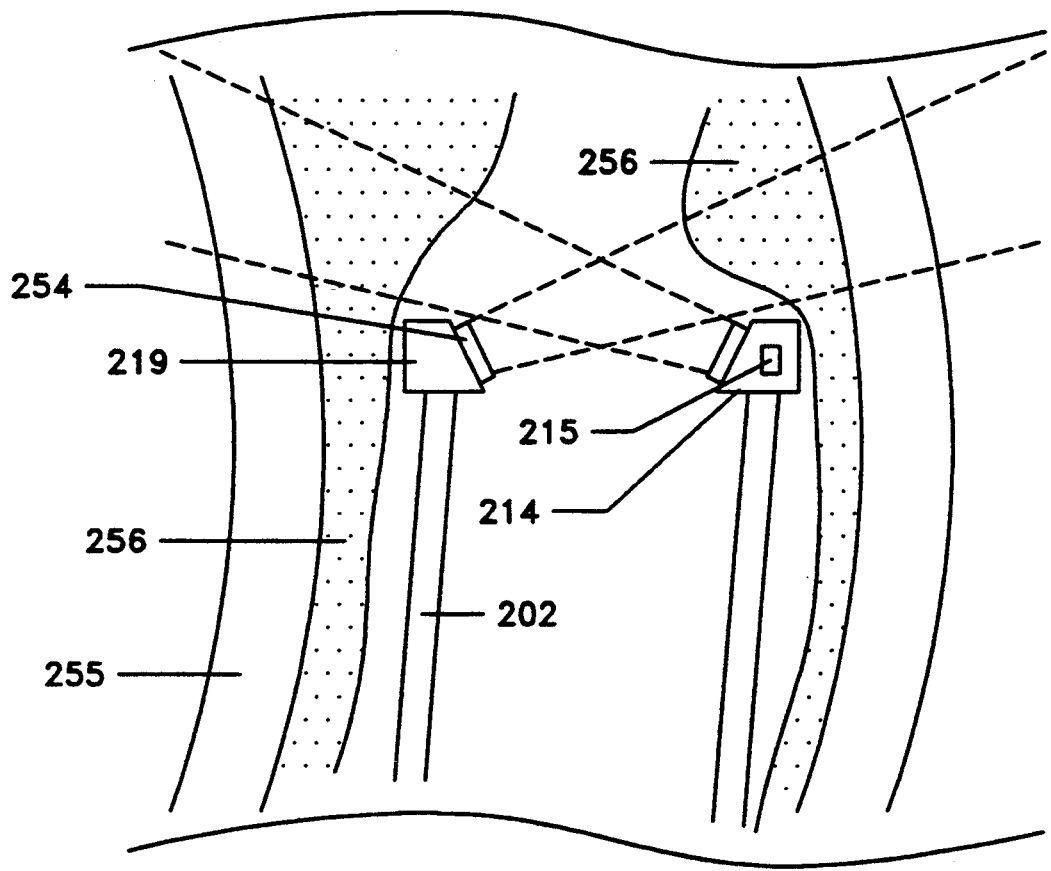
FIG. 23 is a schematic side view of a portion of an area-change section of a robotic snake in a blood vessel showing locations of an imaging system, according to the fourth embodiment of the invention.

FIG. 23 is a schematic side view of a portion of working end area-change section 274 of robotic snake 225 in a blood vessel with blood vessel walls 255, showing locations of perimeter wall imaging elements 254, according to the fourth embodiment of the invention. FIG. 16 shows the location of perimeter imaging elements from a top view. A working end could be either a front or a back of robotic snake 225, depending on the application. Perimeter imaging elements 254 are located on the interior side of base corners 219 or outer telescopic elements 214. An example of perimeter imaging element 254 is an array of ultrasonic imagers which have transmission and receiving capabilities. FIG. 23 shows how perimeter imaging elements probe the region of the interior of the blood vessel, including plaque 256 and blood vessel wall 255, wherein said probed region is immediately beyond working-end area-change section 274, wherein said probed region is on the opposite side of working-end area-change section 274 from the location of the active perimeter imaging element 254. The dashed lines indicate the probed region.

Figure 24:
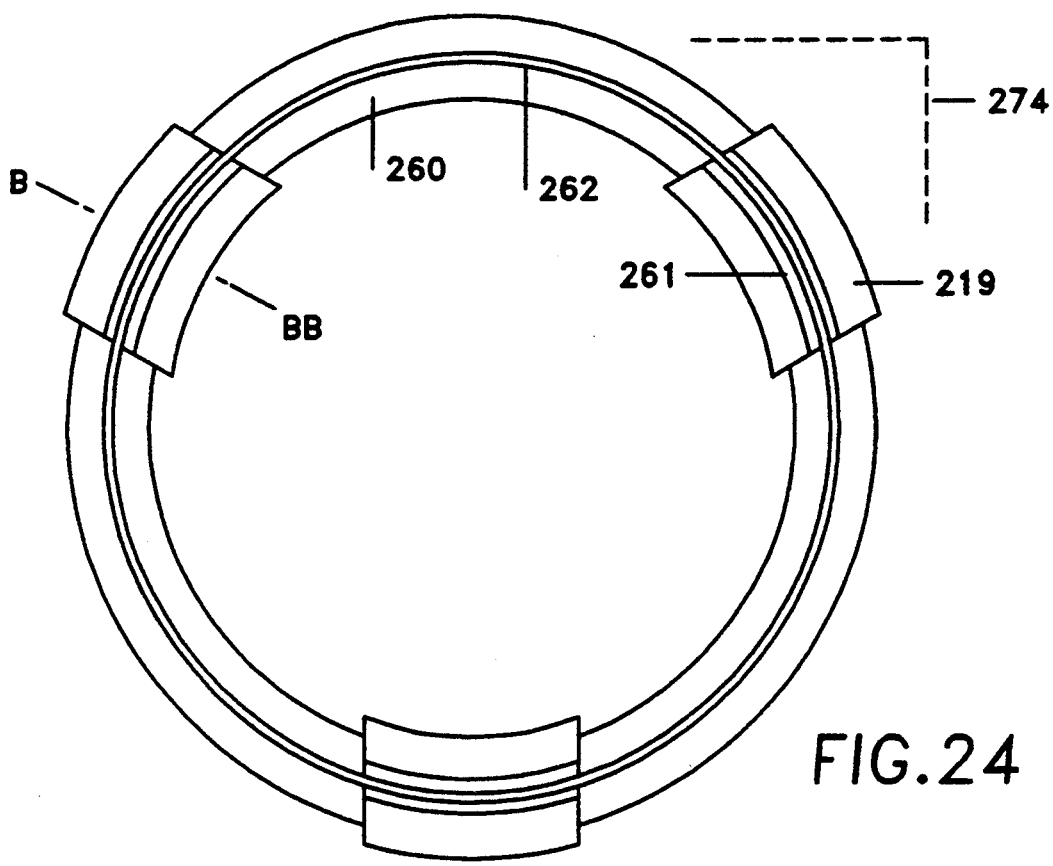
FIG. 24 is a schematic top view of a circular working-end area-change section of a robotic snake showing a fixed cutting hoop on a working-end area-change section of fixed size, according to the fifth embodiment of the invention.

FIG. 24 is a schematic top view of a circular working-end area-change section 274 of robotic snake 225 showing fixed cutting hoop 262 on a working-end area-change section 274 (of fixed size here), according to the fifth embodiment of the invention. The idea of this embodiment is for robotic snake 225 to push fixed cutting hoop 262 to cut its way through any blockage. The cutting action of fixed cutting hoop 262 may be enhanced by a twisting motion of working-end area-change section 274 or by incorporation of a heating element within fixed cutting hoop 262. Also, if a portion of fixed cutting hoop 262 were covered, this portion would not cut; this portion could then be oriented to face a particular side of lumen 299 (see FIG. 33) which is very close to blood vessel wall 255. In this way, one could ensure that this particular side of blood vessel wall 255 is not cut by fixed cutting hoop 262.

Figure 25:
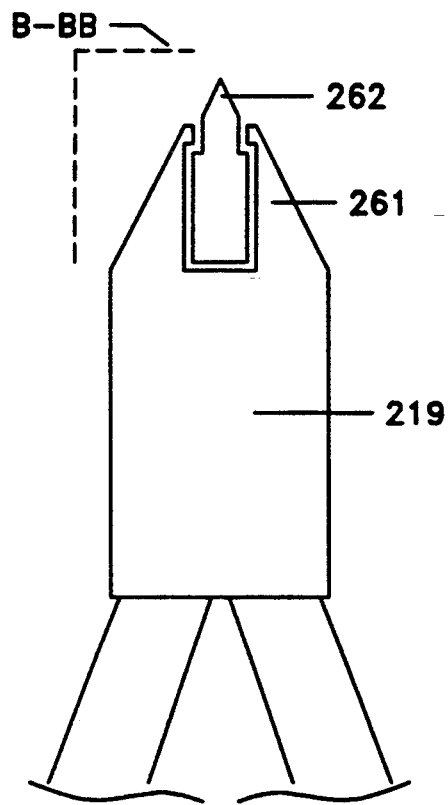
FIG. 25 is a cross-sectional front view of a fixed hoop holder for a circular working-end area-change section of fixed size, according to the fifth embodiment of the invention.

FIG. 25 is a cross-sectional front view of working-end area-change section 274 of robotic snake 225 showing fixed hoop holder 261, according to the fifth embodiment of the invention. Fixed cutting hoop 262 is fixedly attached to fixed hoop holder 261 which forms the top end of base corner 219. Note the wedged shape of the just-mentioned cutting assembly, for easy passage of the entire robotic snake 225 through a tubular cut.

Figure 26:
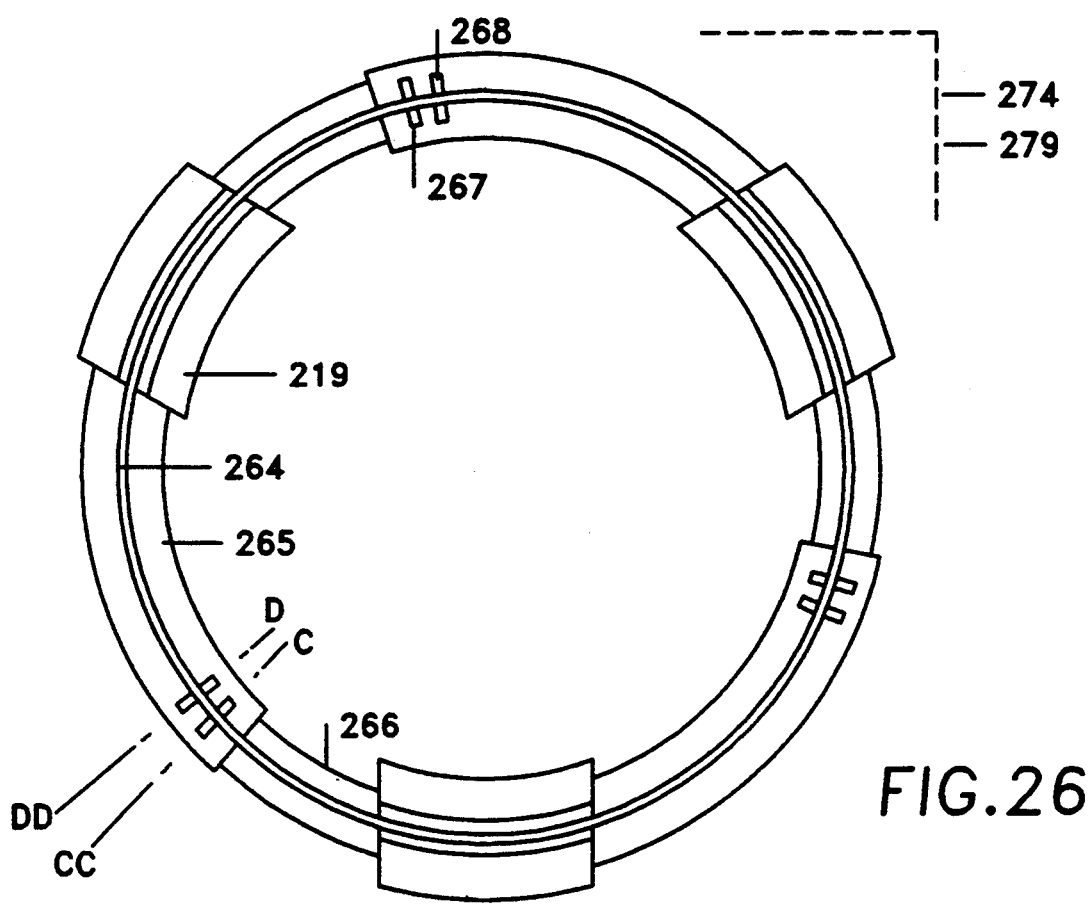
FIG. 26 is a schematic top view of a working-end area-change section of a robotic snake showing a variable cutting hoop assembly on an approximately circular working-end area-change section of variable size, according to the sixth embodiment of the invention.

FIG. 26 is a schematic top view of working-end area-change section 274 of robotic snake 225 showing variable cutting hoop assembly 279 on an approximately circular working-end area-change section 274 of variable size, according to the sixth embodiment of the invention. This variation is complicated by the need for inner base telescopic element 266 to telescopically slide within outer base telescopic element 265. This makes it necessary to have the cutting elements be segments which can overlap as the area of working end area-change section 274 decreases. Each of the 3 variable cutting hoop segments 264 are fixedly attached to a base corner 219 via fixed hoop holder 261, and each is slidingly attached on one side to the adjacent outer base telescopic element 265, first through second hoop guide 268 and second through first hoop guide 267, and on the other side first through first hoop guide 267 and second through second hoop guide 268. This arrangement is necessary because it is not possible to attach a variable cutting hoop segment 264 directly to inner base telescopic element 266.

Figure 27:
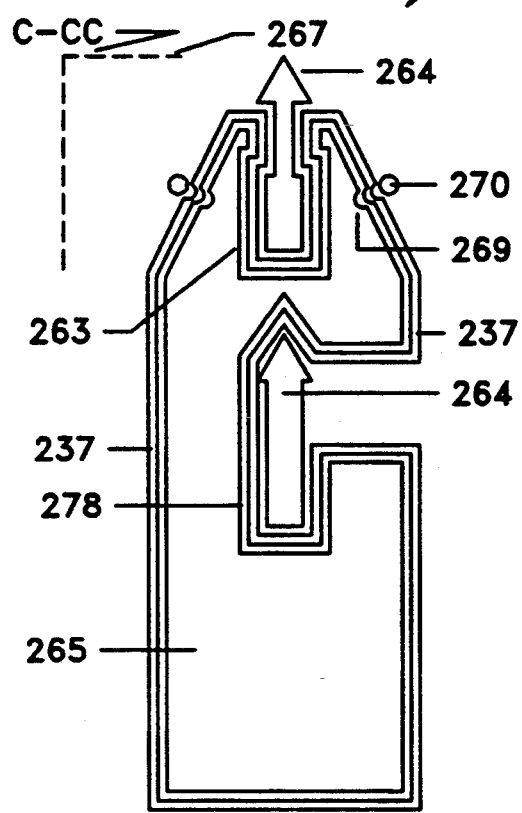
FIG. 27 is a cross-sectional front view of a first hoop guide for a circular working-end area-change section of variable size, according to the sixth embodiment of the invention.

FIG. 27 is a cross-sectional front view of first hoop guide 267 for a circular working-end area-change section 274 of variable size, according to the sixth embodiment of the invention. First hoop guide 267 forms the upper portion of outer base telescopic element 265; alternatively it could be fixedly attached to outer base telescopic element 265. First hoop guide 267 comprises first upper slot 263 through which passes a first variable hoop segment 264 and a first lower slot 278 through which a second variable hoop segment 264 passes. Elastic skin 237 surrounds outer and inner base telescopic elements 265 and 266 for protection against the environment.

Figure 28:
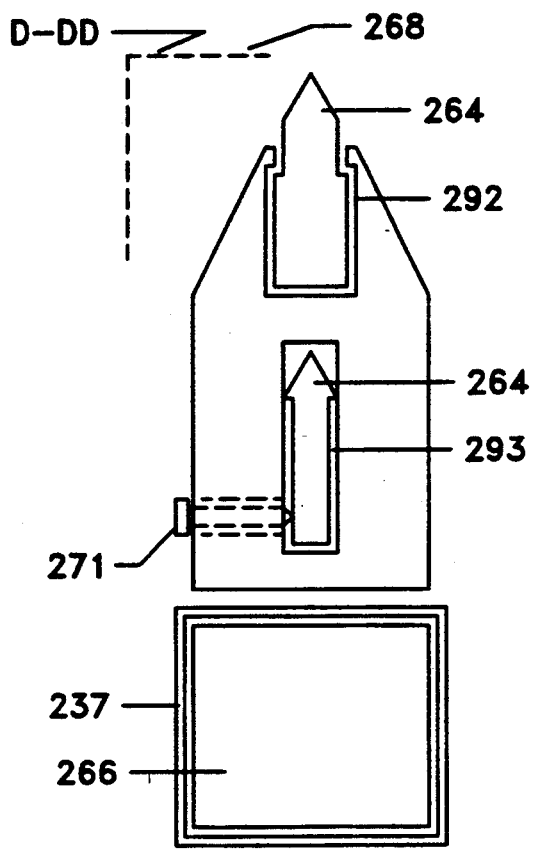
FIG. 28 is a cross-sectional front view of a second hoop guide for a circular working-end area-change section of variable size, according to the sixth embodiment of the invention.

FIG. 28 is a cross-sectional front view of second cutting hoop guide 268 for a circular working-end area-change section 274 of variable size, according to the sixth embodiment of the invention. Second hoop guide 268 comprises second upper slot 292 through which passes a first variable hoop segment 264 and a second lower slot 293 through which a second variable hoop segment 264 passes. Second hoop guide is fixedly attached to a second variable hoop segment 264 via guide screw 271. An additional and optional feature is elastic skin 237.

FIG. 29 is a front view of hot-wire cutting hoop 294 of robotic snake 225 showing an insulating layer, according to the sixth embodiment of the invention. Hot-wire cutting hoop 294 comprises resistive cutting element 290 for electrical resistive heating and insulator layer 291. This hot-wire feature enhances the cutting action of, e.g., fixed cutting hoop 262. In a blood vessel it also paves the interior of the blood vessel after the cut has been made, thereby reducing the chance of restenosis.

FIG. 30 is a side view of saw-tooth cutting hoop 295 of robotic snake 225 showing saw-tooth edge 289, according to the sixth embodiment of the invention. By invoking a twisting action of working-end area-change section 274, saw-tooth edge 289 enhances the cutting action of the device.

FIG. 31 is a profile side view and FIG. 32 is a top view of penetration tool 296 of robotic snake 225, according to the seventh embodiment of the invention. The purpose of this tool is to make a cylindrically symmetric array of radial cuts in a region of blockage within a blood vessel, thereby allowing penetration of robotic snake 225 through said blockage with a minimum of risk of a radial cut or a crack extending to cause a lesion in the vessel wall. Penetration tool 296 comprises penetration cone 275 which is fixedly attached to the front end of robotic snake 225, which incorporates flow holes 277, and which incorporates cone knife edges 276, which are oriented perpendicular to the surface of penetration cone 275. Outer elastic skin 22 acts as a sack to prevent any plaque debris from escaping from the interior of robotic snake 225, and flow holes 277 allow blood to flow through the interior of robotic snake 225. An array of internal imagers 288 give mapping information for a penetration in which trajectory Ts of robotic snake 225 is continually aligned with trajectory Tw of blood vessel wall 255.

Figure 33:
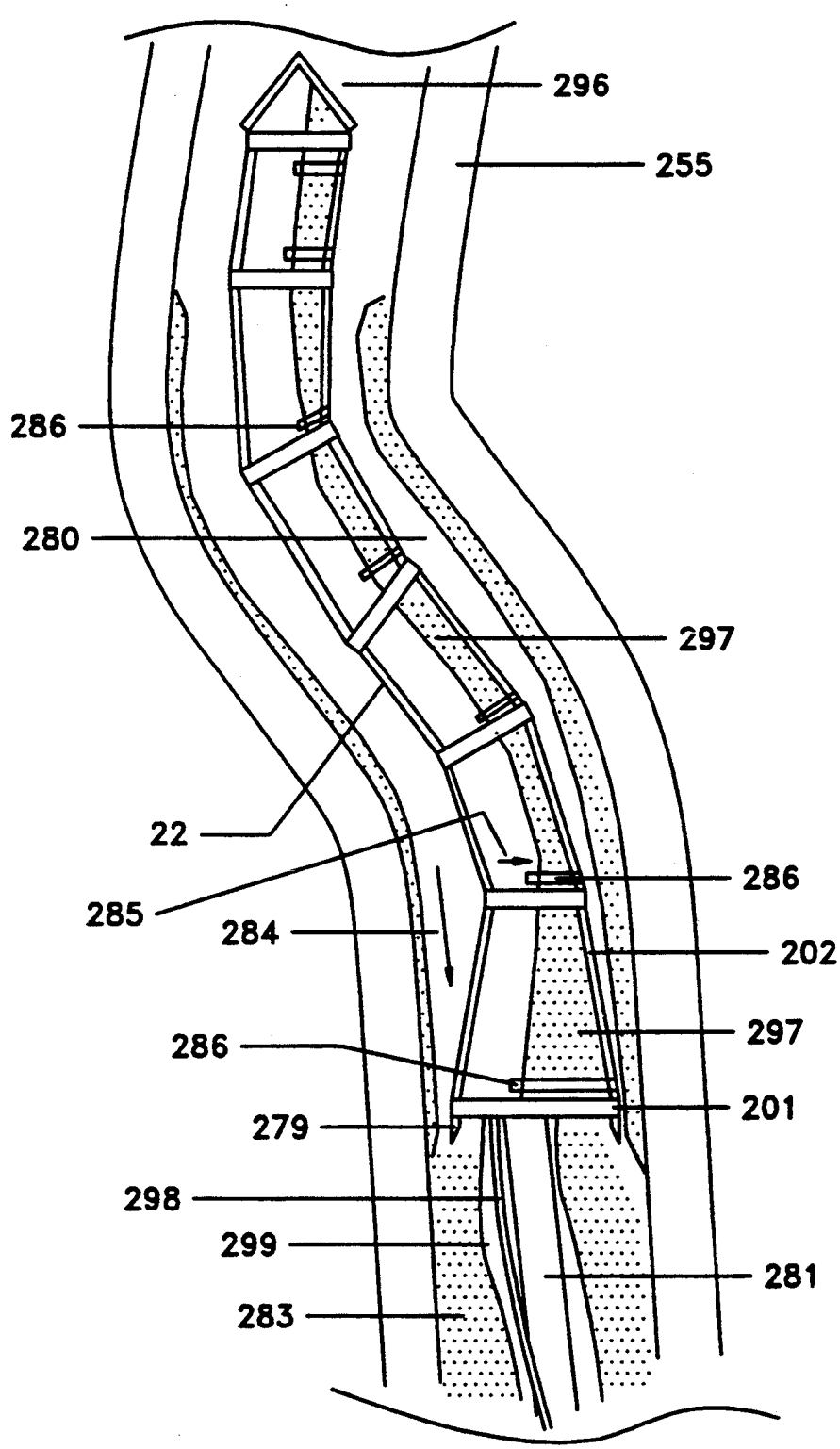
FIG. 33 is a side view of a robotic snake incorporating a penetrating tool and a cutting hoop, according to the sixth and seventh embodiments of the invention.

FIG. 33 is a side view of robotic snake 225 incorporating penetration tool 296 and variable cutting hoop assembly 279, according to the sixth and seventh embodiments of the invention. It should be understood that fixed cutting hoop 262 could be use as well. The objective of this combination of embodiments is for robotic snake 225 to first penetrates to the other side of a region, indicated by plaque 283, of partial or complete blockage of a blood vessel. Penetration tool 296 leads this penetration. Then, the direction of self-propulsion is reversed, and variable cutting hoop assembly 279 expands to a desired size and robotic snake 225 returns in the direction of arrow 284 through the region of plaque 283, thereby cutting a lumen bounded by paved plaque 280. Plaque debris 297 is gathered in and contained within outer elastic skin 22 of robotic snake 225. Additional pulling power for the return pass can be accomplished via guide wire 281 which would be inserted through the penetration lumen and which either could grapple an internal area-change section 201 or could be gripped by an area-change section 201.

FIG. 33 also shows a cable scheme to compress plaque debris 297 on one side of the interior of robotic snake 225, according to the seventh embodiment of the invention. Initially, a plurality of cable loops 286 extend all the way around the interior of robotic snake on the loop end and out to the exterior of the patient. The ends of cable loops 286 can be drawn to compress plaque debris 297 against one side of the interior of robotic snake 225, thereby allowing blood to freely flow throughout the interior of robotic snake 225.

Figure 34:
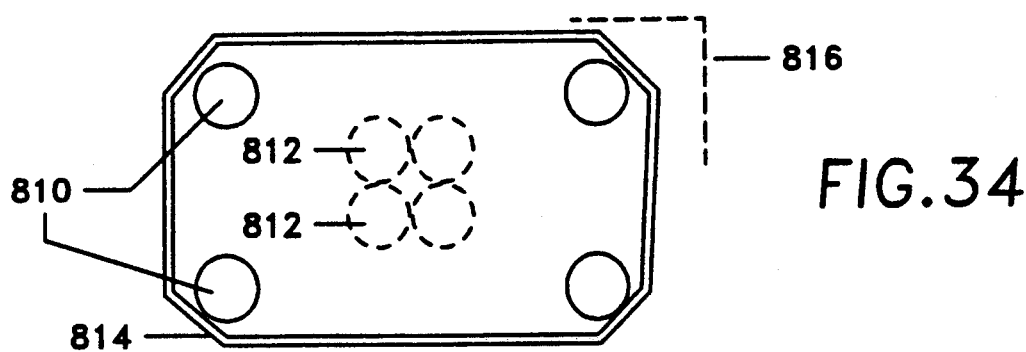
FIG. 34 is a top view of a multi-fingered working end of a robotic snake, according to the eighth embodiment of the invention.
Figure 35:
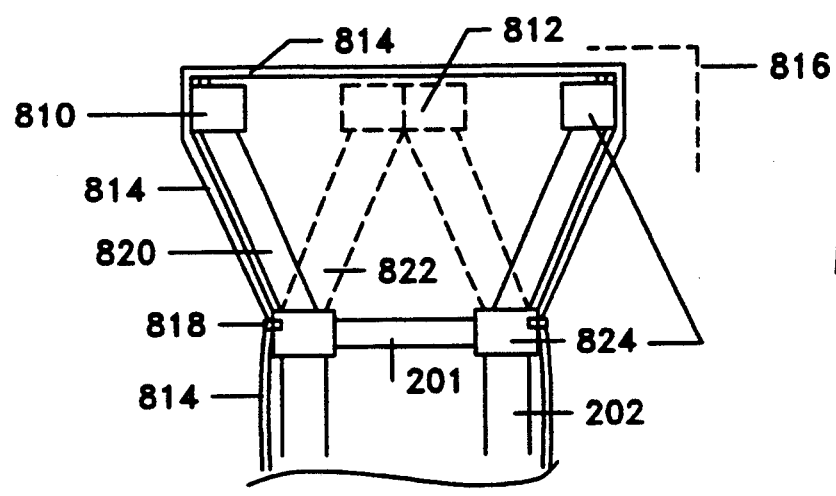
FIG. 35 is a side view of a multi-fingered working end of a robotic snake, according to the eighth embodiment of the invention.

FIG. 34 is a top view and FIG. 35 a side view of multi-fingered working end 816 of robotic snake 225, according to the eighth embodiment of the invention. Each robo-finger length-change element 820 comprises six length actuators 211 (refer to FIGS. 9-11), connected on either end to robo-finger bases 824 via universal joints. Thus, each robo-finger length-change element 820 can move independently. This independent motion is indicated by the positions in closed position (shown in phantom) of robo-finger length-change elements 812. This movement allows a large range of sizes and shapes for the perimeter formed by the ends of robo-fingers 810, which are optionally connected by cutting wire 814 which, in turn, passes via cutting wire restraints 818 to a reel mechanism external to robo-snake 225. This reel mechanism maintains cutting wire 814 taut as robo-fingers 810 move. Robo-fingers 810 (there may be one or more) extend from the working end of robo-snake 225.

Figure 36:
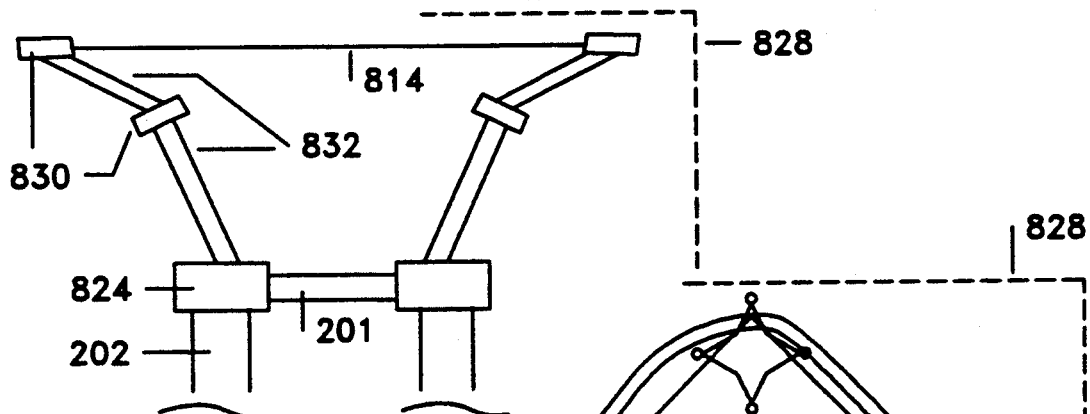
FIG. 36 is a side view of a multi-sectioned, multi-fingered working end of a robotic snake, according to the eighth embodiment of the invention.
Figure 37:
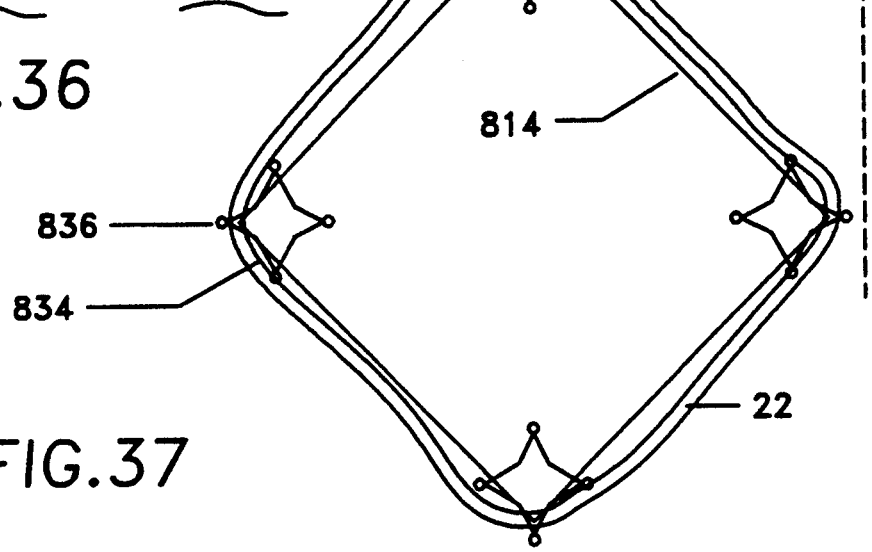
FIG. 37 is a top view of a multi-sectioned, multi-fingered working end of a robotic snake, according to the eighth embodiment of the invention.

FIG. 36 is a side view and FIG. 37 a top view of multi-sectioned robo-fingers 828 of multi-fingered working end 816 of robotic snake 225, according to the eighth embodiment of the invention. In effect, each robo-finger 810 of FIG. 34 now becomes multi-sectioned robo-finger 828, which, by itself, is equivalent to robo-snake 225. Robo-finger multi-section length-change elements 832 now connect multi-sectioned robo-finger bases 830, one of which is connected to robo-finger base 824 which forms the end of robo-snake 225. The only reason for multiple sections is to achieve a greater range of size change than for a given total length of robo-finger 810.

FIG. 37 shows a means to remove sections of tissue in microsurgery by having each side of the multi-sectioned robo-finger 828 (or robo-finger 810) capable of cutting tissue. Lengthwise cutting edges 834 and lengthwise cutting wires 836 extend along multi-sectioned robo-finger length-change elements 832, which may be connected web-fashion to an elastic skin such as outer elastic skin 22 in FIG. 5. These features, combined with the capability of twisting of multi-fingered working end 816 about its longitudinal axis permit coring of tissue as well as scooping of cores of arbitrary shape and size. Furthermore, the capability of closing multi-fingered working end 816 when cutting is complete, allows these cores or this debris to be captured within robotic snake 225 for safe removal.

The next section addresses the issue of signal transmission to and from the length actuators which are the basic structural element of the robo-snake. Although separate wires could, in principle, be used for each signal transmitted, this would quickly become cumbersome. A multiplexing solution is included here as a design which requires a minimal number of wires. At each stage 226, there will be stage circuitry 800 to perform the necessary switching to activate the various components in the actuators.

Two basic types of signal transmission systems are envisioned. These depend on the nature of voltages required by an actuator. The first signal transmission type could be used with two of the afore-mentioned kinds of actuators which are described in co-pending applications, namely the inchworm linear motor or the free-standing, traveling-wave ultrasonic linear motor. These require a particular sequence of voltages to various components (to be enacted by logic at the actuator site), and their total length change depends primarily on the time of activation. The second signal transmission type could be used with the afore-mentioned micromachined actuator which is also co-pending. In this case, the actuator length change is primarily a function of the imposed voltage, which means that less logic "real estate" is required at the actuator site. The basic circuits for these two signal transmission types are described below.

Figure 38:
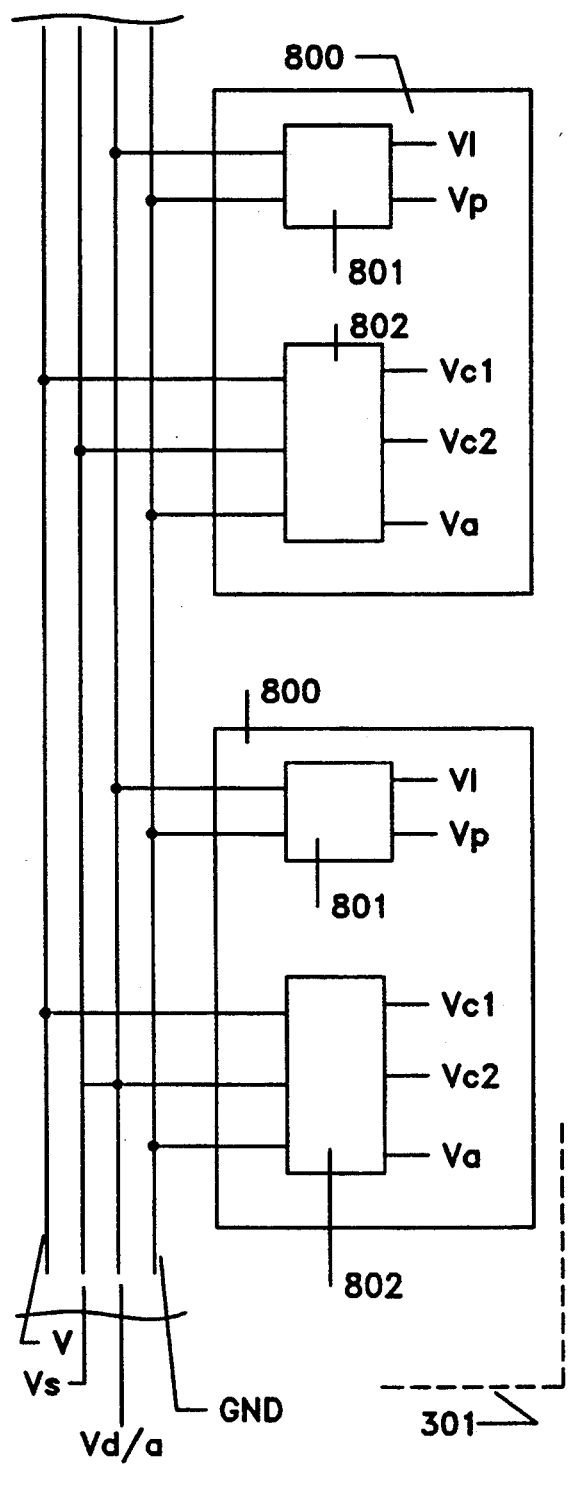
FIG. 38 is a schematic of a first signal transmission system of a robotic snake, according to the first embodiment of the invention.

FIG. 38 shows first signal transmission system 805 of inchworm actuator 301, according to the first embodiment of the invention. Each stage circuitry 800 comprises D/A switching system 801 which allows line voltage $V_{d/a}$ to sense $V_l$ and $V_p$, the signal voltages from a length sensor and a pressure sensor in inchworm actuator 301. Each stage circuitry 800 further comprises actuation switching system 802 which sends particular sequences of voltages $V_{c1}$ and $V_{c2}$ to a clamping system and particular sequences of voltages $V_a$ to an actuation system in inchworm actuator 301. $V_s$ triggers this sequence and V represents power supply voltage.

The four lines: V, $V_s$, $V_{d/a}$, and GND, extend from the last stage 226 of robotic snake 225 through each other stage 226, and then along trail wires 298 (see FIG. 33) out to a control system external to the region of application of robotic snake 225. In this way, each actuator of robotic snake 225 has an independent control.

Figure 39:
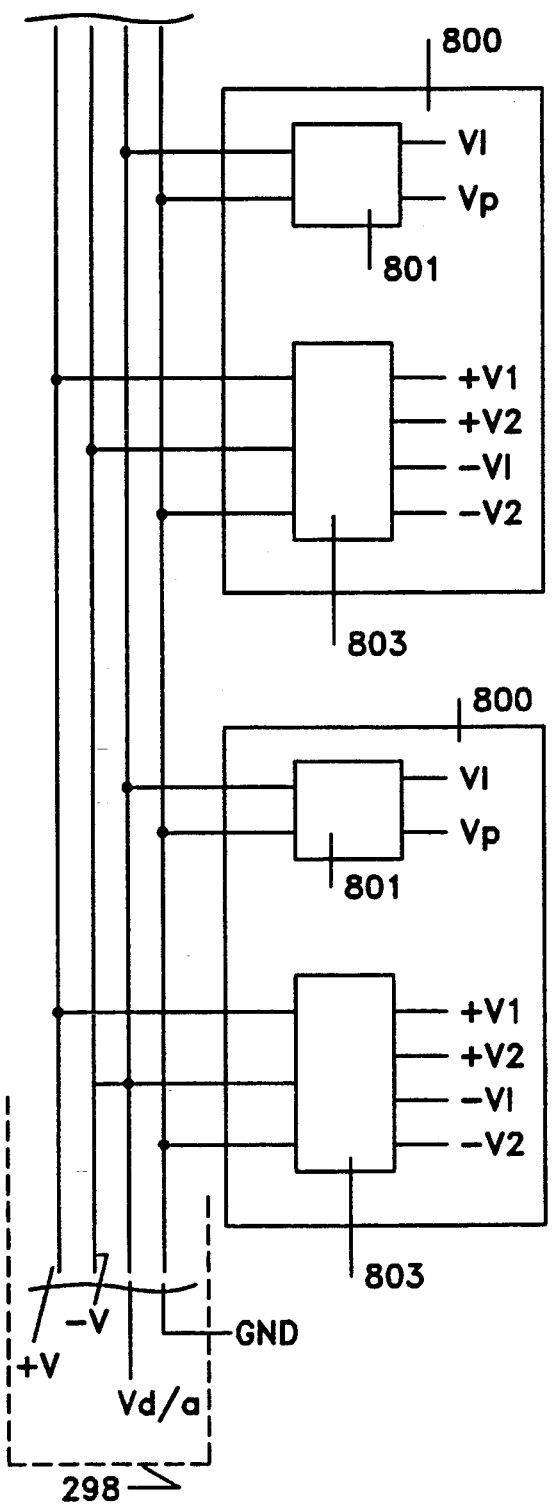
FIG. 39 is a schematic of a second signal transmission system of a robotic snake, according to the first embodiment of the invention.

FIG. 39 shows a schematic of second signal transmission system 804 for control of micro-actuator array 1 of robotic snake 225, according to the first embodiment of the invention. Each stage circuitry 800 comprises D/A switching system 801 which allows line $V_{d/a}$ to sense $V_1$ and $V_p$, the signal voltages from a length sensor and a pressure sensor in micro-actuator 1. Each stage circuitry 800 further comprises voltage-divider/actuation switching system 802 which converts line voltages +V and −V to the various busline voltages ±V1 and ±V2, according to various sequences required to cause a particular length change by micro-actuator 1. In this way, each actuator in robotic snake 225 has an independent control.

The four lines: +V, −V, $V_{d/a}$, and GND, extend from the last stage 226 of robotic snake 225 through each other stage 226, and then along trail wire 298 out to a control system external to the region of application of robotic snake 225.

The above description shall not be construed as limiting the ways in which this invention may be practiced but shall be inclusive of many other variations that do not depart from the broad interest and intent of the invention.

Having thus described the invention, what is claimed as new and desired to be secured by Letters Patent is:

1. A robotic snake comprising:
   a plurality of articulation units, serially connected, including a top articulation unit and a bottom articulation unit wherein:
   each of said articulation units comprises a rear section, a fore section, and a lengthwise interconnect section, wherein the fore section of one of said articulation units comprises the rear section of the succeeding articulation unit, and wherein said rear section and said fore section are rotatable relative to each other, wherein said rear section and said fore section are equivalent structures except for positional considerations within said robotic snake and the general term for rear section or base section is defined to be base section,
   said rear section comprising three base joint vertices interconnected by three base interconnect elements,
   said fore section comprising three base joint vertices interconnected by three base interconnect elements,
   said lengthwise interconnect section comprising six lengthwise actuators, also referred to as actuators, wherein each of said base joint vertices of said rear section is coupled to two of said lengthwise actuators and each of said two lengthwise actuators is coupled to a different one of said base joint vertices of said fore section,
   a sensor system for interrogation of the surrounding environment and for determination of the location of said robotic snake with respect to said surrounding environment,
   a control system, and
   a signal transmission system, wherein said control system incorporates information from said sensor system to cause electrical signals to be sent via said signal transmission system to activate said lengthwise actuators to achieve a pre-determined motion of said robotic snake.

2. The robotic snake of claim 1 wherein each of said base joint vertices comprises a joint plate and four universal joints, except that each of said base joint vertices of said rear section of said bottom articulation unit comprises a joint plate and two universal joints, and except that each of said base joint vertices of said fore section of said top articulation unit comprises a joint plate and two universal joints, wherein each of said lengthwise actuators is coupled to a corresponding one of said universal joints.

3. The robotic snake of claim 2, wherein each of said base interconnect elements is a base actuator and each of said base joint vertices further comprises two base pivots, each of which is coupled to one of said base actuators, wherein said base actuator is often equivalent in structure to said length actuator in which case the term actuator is used to refer to either said lengthwise actuator or said base actuator.

4. The robotic snake of claim 1 wherein each of said base interconnect elements or each of said lengthwise actuators is arcuate in length.

5. The robotic snake of claim 1 wherein one of the cross-sectional dimensions, namely the actuator width, of said actuator is greater than the other cross-sectional dimension, namely the actuator depth.

6. The robotic snake of claims 1 wherein each of said actuators has a cross-section which is arcuate.

7. The robotic snake of claim 2, wherein each of said universal joints comprises a monolithic pivot further comprising:
   an upper end,
   a lower end, and
   a mid-portion also referred to as a universal neck, wherein said universal neck is sufficiently smaller in cross-sectional area than said upper end or said lower end to permit free and universal rotation of said upper end with respect to said lower end.

8. The robotic snake of claim 2, wherein each of said universal joints comprises a bellows joint.

9. The robotic snake of claim 2, wherein each of said universal joints comprises:
   an upper end,
   a lower end, and
   a mid-portion comprising a flexible tube connecting said upper and lower ends.

10. The robotic snake of claim 1, wherein said sensor system comprises one or more pressure sensors.

11. The robotic snake of claim 1 wherein said sensor system comprises one or more length sensors.

12. The robotic snake of claim 1, wherein at least one end of said robotic snake, which could be said top articulation unit or said bottom articulation unit, further comprises a tool.

13. The robotic snake of claim 1, wherein at least one end of said robotic snake, which could be said top articulation unit or said bottom articulation unit, has a different size than its neighboring articulation units.

14. The robotic snake of claim 1 wherein said actuator is covered with an elastic skin.

15. The robotic snake of claim 3, wherein each of said base pivots is a monolithic hinge.

16. The robotic snake of claim 1 wherein said actuator further comprises an outer telescopic element and an inner telescopic element.

17. The robotic snake of claim 16, wherein said outer telescopic element further comprises a external cladding.

18. The robotic snake of claim 1, wherein said control system comprises a second robotic snake called a master robotic snake which has the same structure as said robotic snake, wherein said master robotic snake experiences external forces causing the initiation of motion of said master actuators, wherein said control system causes said robotic snake to initiate motion of all component ones of said actuators which motion mimics the motion of said master actuators, wherein said control system causes said master robotic snake to limit the motion of said actuators to motion equivalent to motion of said master actuators, wherein a person who manipulates said master robotic snake can sense forces equivalent to forces which are acting on said robotic snake by said surrounding environment.

19. The robotic snake of claim 1, wherein said sensor system comprises an imaging system.

20. The robotic snake of claim 12, wherein said tool comprises an ultrasonic imaging system.

21. The robotic snake of claim 19, wherein said imaging system comprises an ultrasonic imaging system which further comprises an array of ultrasonic elements which transmit and receive ultrasonic waves.

22. The robotic snake of claim 21, wherein said imaging system is located on the perimeter of one or more of said base sections.

23. The robotic snake of claim 12, wherein said tool comprises a cutting hoop.

24. The robotic snake of claim 23, wherein said cutting hoop comprises a variable cutting hoop further comprising:
   three fixed hoop holders fixedly attached to said base corners,
   three variable cutting hoop segments each of which is fixedly attached at its mid-point to one of said fixed hoop holders,
   three first hoop guides each of which is fixedly attached to said outer telescopic element,
   three second hoop guides each of which is fixedly attached to one of said cutting hoop segments, wherein each of two different said cutting hoop segments is guided slidingly through each said first hoop guide and wherein each of said cutting hoop segments is guided slidingly through said second hoop guide.

25. The robotic snake of claim 23, wherein said cutting hoop comprises a heater.

26. The robotic snake of claim 25, wherein said heater is a resistive heater.

27. The robotic snake of claim 23, wherein said cutting hoop comprises a saw-tooth edge.

28. The robotic snake of claim 12, wherein said tool comprises a penetration tool.

29. The robotic snake of claim 29, wherein said penetration tool comprises:
   a penetration cone fixedly attached to said end, wherein said penetration cone may be perforated,
   an array of cone knife edges fixedly attached to said penetration cone, and
   an array of internal imagers fixedly attached to said penetration cone.

30. The robotic snake of claim 1, wherein said signal transmission system further comprises a multiplexing system.

31. The robotic snake of claim 1, wherein said multiplexing system comprises:
   an actuation system located at the site of each of said lengthwise actuators for the purpose of sending the particular sequence of electrical signals needed to cause a prescribed length change in said lengthwise actuator,
   a digital-to-analog (D/A) switching system located at the site of said lengthwise actuators for the purpose of converting analog signals form said sensor system to digital signals to be sent to said control system,
   a wiring system connecting said control system with said actuation system and said D/A switching system.

32. The robotic snake of claim 3, wherein said multiplexing system comprises:
   an actuation system located at the site of each of said base actuators for the purpose of sending the particular sequence of electrical signals needed to cause a prescribed length change in said base actuator,
   a digital-to-analog (D/A) switching system located at the site of said base actuators for the purpose of converting analog signals form said sensor system to digital signals to be sent to said control system,
   a wiring system connecting said control system with said actuation system and said D/A switching system.

33. The robotic snake of claim 12, wherein said tool comprises a plurality of robotic fingers, each of which further comprises one or more articulation units, serially connected, including a top articulation unit and a bottom articulation unit wherein:
   each of said articulation units comprises a rear section, a fore section, and a lengthwise interconnect section, wherein the fore section of one of said articulation units comprises the rear section of the succeeding articulation unit, and wherein said rear section and said fore section are rotatable relative to each other, wherein said rear section and said fore section are equivalent structures except for positional considerations within said robotic snake and the general term for rear section or base section is defined to be base section,
   said rear section comprising three base joint vertices interconnected by three base interconnect elements,
   said fore section comprising three base joint vertices interconnected by three base interconnect elements,
   said lengthwise interconnect section comprising six lengthwise actuators, also referred to as actuators, wherein each of said base joint vertices of said rear section is coupled to two of said lengthwise actuators and each of said two lengthwise actuators is coupled to a different one of said base joint vertices of said fore section,
   a sensor system for interrogation of the surrounding environment and for determination of the location of said robotic snake with respect to said surrounding environment,
   a control system, and
   a signal transmission system, wherein said control system incorporates information from said sensor system to cause electrical signals to be sent via said signal transmission system to activate said lengthwise actuators to achieve a pre-determined motion of said robotic finger.

* * * * *